(12) United States Patent
Goodman et al.

(10) Patent No.: US 6,270,995 B1
(45) Date of Patent: Aug. 7, 2001

(54) RECOMBINANT POLYNUCLEOTIDES ENCODING A SLIT POLYPEPTIDE

(75) Inventors: Corey S. Goodman; Thomas Kidd, both of Berkeley; Katja Brose; Marc Tessier-Lavigne, both of San Francisco, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/540,153

(22) Filed: Mar. 31, 2000

Related U.S. Application Data

(62) Division of application No. 09/191,647, filed on Nov. 13, 1998, now Pat. No. 6,046,015.
(60) Provisional application No. 60/081,057, filed on Apr. 7, 1998, and provisional application No. 60/065,544, filed on Nov. 14, 1997.
(51) Int. Cl.[7] ............................. C12P 21/02; C07H 21/04
(52) U.S. Cl. ........................................ 435/69.1; 536/23.5
(58) Field of Search ........................... 536/23.5; 435/69.1

(56) References Cited

PUBLICATIONS

Hillier et al, Locus AA055976 of the Embl–est58 and Genbank–est111 databases, unnumbered page, Feb. 1, 1997.*

Hillier et al, Locus R78732 of the Embl–est58 and Genbank–est11 databases, unnumbered page, Jun. 9, 1995.*

Wilson et al., Nature, vol. 368: pp. 32–38. (Mar. 3, 1994).

* cited by examiner

*Primary Examiner*—Terry McKelvey
(74) *Attorney, Agent, or Firm*—Richard Aron Osman

(57) ABSTRACT

Disclosed are methods and compositions for identifying agents which modulate the interaction of Robo and a Robo ligand and for modulating the interaction of Robo and a Robo ligand. The methods for identifying Robo:ligand modulators find particular application in commercial drug screens. These methods generally comprise (1) combining a Robo polypeptide, a Slit polypeptide and a candidate agent under conditions whereby, but for the presence of the agent, the Robo and Slit polypeptides engage in a first interaction, and (2) determining a second interaction of the Robo and Slit polypeptides in the presence of the agent, wherein a difference between the first and second interactions indicates that the aget modulates the interaction of the Robo and Slit polypeptides. The subject methods of modulating the interaction of Robo and a Robo ligand involve combining a Robo polypeptide, a Slit polypeptide and a modulator under conditions whereby, but for the presence of the modulator, the Robo and Slit polypeptides engage in a first interaction, whereby the Robo and Slit polypeptides engage in a second interaction different from the first interaction. In a particular embodiment, the modulator is dominant negative form of the Robo or Slit polypeptide.

19 Claims, No Drawings

SEQUENCE LISTING

<160> NUMBER OF SEQ ID NOS: 14

<210> SEQ ID NO 1
<211> LENGTH: 4758
<212> TYPE: DNA
<213> ORGANISM: human
<220> FEATURE:
<221> NAME/KEY: CDS
<222> LOCATION: (1)..(4575)

<400> SEQUENCE: 1

```
atg cgc ggc gtt ggc tgg cag atg ctg tcc ctg tcg ctg ggg tta gtg      48
Met Arg Gly Val Gly Trp Gln Met Leu Ser Leu Ser Leu Gly Leu Val
 1               5                  10                  15 ctg gcg atc ctg aac aag gtg gca ccg cag gcg tgc ccg gcg cag tgc      96
Leu Ala Ile Leu Asn Lys Val Ala Pro Gln Ala Cys Pro Ala Gln Cys
             20                  25                  30
```

-continued

| | | |
|---|---|---|
| tct tgc tcg ggc agc aca gtg gac tgt cac ggg ctg gcg ctg cgc agc<br>Ser Cys Ser Gly Ser Thr Val Asp Cys His Gly Leu Ala Leu Arg Ser<br>          35                   40                    45 | 144 |
| gtg ccc agg aat atc ccc cgc aac acc gag aga ctg gat tta aat gga<br>Val Pro Arg Asn Ile Pro Arg Asn Thr Glu Arg Leu Asp Leu Asn Gly<br>50                     55                    60 | 192 |
| aat aac atc aca aga att acg aag aca gat ttt gct ggt ctt aga cat<br>Asn Asn Ile Thr Arg Ile Thr Lys Thr Asp Phe Ala Gly Leu Arg His<br>65                    70                  75                80 | 240 |
| cta aga gtt ctt cag ctt atg gag aat aag att agc acc att gaa aga<br>Leu Arg Val Leu Gln Leu Met Glu Asn Lys Ile Ser Thr Ile Glu Arg<br>               85                    90                  95 | 288 |
| gga gca ttc cag gat ctt aaa gaa cta gag aga ctg cgt tta aac aga<br>Gly Ala Phe Gln Asp Leu Lys Glu Leu Glu Arg Leu Arg Leu Asn Arg<br>              100                 105               110 | 336 |
| aat cac ctt cag ctg ttt cct gag ttg ctg ttt ctt ggg act gcg aag<br>Asn His Leu Gln Leu Phe Pro Glu Leu Leu Phe Leu Gly Thr Ala Lys<br>              115                 120               125 | 384 |
| cta tac agg ctt gat ctc agt gaa aac caa att cag gca atc cca agg<br>Leu Tyr Arg Leu Asp Leu Ser Glu Asn Gln Ile Gln Ala Ile Pro Arg<br>130                    135                 140 | 432 |
| aaa gct ttc cgt ggg gca gtt gac ata aaa aat ttg caa ctg gat tac<br>Lys Ala Phe Arg Gly Ala Val Asp Ile Lys Asn Leu Gln Leu Asp Tyr<br>145                   150               155               160 | 480 |
| aac cag atc agc tgt att gaa gat ggg gca ttc agg gct ctc cgg gac<br>Asn Gln Ile Ser Cys Ile Glu Asp Gly Ala Phe Arg Ala Leu Arg Asp<br>                  165               170              175 | 528 |
| ctg gaa gtg ctc act ctc aac aat aac aac att act aga ctt tct gtg<br>Leu Glu Val Leu Thr Leu Asn Asn Asn Asn Ile Thr Arg Leu Ser Val<br>              180                 185               190 | 576 |
| gca agt ttc aac cat atg cct aaa ctt agg act ttt cga ctg cat tca<br>Ala Ser Phe Asn His Met Pro Lys Leu Arg Thr Phe Arg Leu His Ser<br>              195                 200               205 | 624 |
| aac aac ctg tat tgt gac tgc cac ctg gcc tgg ctc tcc gac tgg ctt<br>Asn Asn Leu Tyr Cys Asp Cys His Leu Ala Trp Leu Ser Asp Trp Leu<br>210                    215                 220 | 672 |
| cgc aaa agg cct cgg gtt ggt ctg tac act cag tgt atg ggc ccc tcc<br>Arg Lys Arg Pro Arg Val Gly Leu Tyr Thr Gln Cys Met Gly Pro Ser<br>225                   230               235               240 | 720 |
| cac ctg aga ggc cat aat gta gcc gag gtt caa aaa cga gaa ttt gtc<br>His Leu Arg Gly His Asn Val Ala Glu Val Gln Lys Arg Glu Phe Val<br>              245                 250               255 | 768 |
| tgc agt gat gag gaa gaa ggt cac cag tca ttt atg gct cct tct tgt<br>Cys Ser Asp Glu Glu Glu Gly His Gln Ser Phe Met Ala Pro Ser Cys<br>260                    265                 270 | 816 |
| agt gtt ttg cac tgc cct gcc gcc tgt acc tgt agc aac aat atc gta<br>Ser Val Leu His Cys Pro Ala Ala Cys Thr Cys Ser Asn Asn Ile Val<br>              275                 280               285 | 864 |
| gac tgt cgt ggg aaa ggt ctc act gag atc ccc aca aat ctt cca gag<br>Asp Cys Arg Gly Lys Gly Leu Thr Glu Ile Pro Thr Asn Leu Pro Glu<br>290                    295                 300 | 912 |
| acc atc aca gaa ata cgt ttg gaa cag aac aca atc aaa gtc atc cct<br>Thr Ile Thr Glu Ile Arg Leu Glu Gln Asn Thr Ile Lys Val Ile Pro<br>305                    310                 315               320 | 960 |
| cct gga gct ttc tca cca tat aaa aag ctt aga cga att gac ctg agc<br>Pro Gly Ala Phe Ser Pro Tyr Lys Lys Leu Arg Arg Ile Asp Leu Ser<br>              325                 330               335 | 1008 |
| aat aat cag atc tct gaa ctt gca cca gat gct ttc caa gga cta cgc<br>Asn Asn Gln Ile Ser Glu Leu Ala Pro Asp Ala Phe Gln Gly Leu Arg<br>              340                 345               350 | 1056 |

```
tct ctg aat tca ctt gtc ctc tat gga aat aaa atc aca gaa ctc ccc      1104
Ser Leu Asn Ser Leu Val Leu Tyr Gly Asn Lys Ile Thr Glu Leu Pro
        355                 360                 365 aaa agt tta ttt gaa gga ctg ttt tcc tta cag ctc cta tta ttg aat      1152
Lys Ser Leu Phe Glu Gly Leu Phe Ser Leu Gln Leu Leu Leu Asn
370                 375                 380 gcc aac aag ata aac tgc ctt cgg gta gat gct ttt cag gat ctc cac      1200
Ala Asn Lys Ile Asn Cys Leu Arg Val Asp Ala Phe Gln Asp Leu His
385                 390                 395                 400 aac ttg aac ctt ctc tcc cta tat gac aac aag ctt cag acc atc gcc      1248
Asn Leu Asn Leu Leu Ser Leu Tyr Asp Asn Lys Leu Gln Thr Ile Ala
                405                 410                 415 aag ggg acc ttt tca cct ctt cgg gcc att caa act atg cat ttg gcc      1296
Lys Gly Thr Phe Ser Pro Leu Arg Ala Ile Gln Thr Met His Leu Ala
                420                 425                 430 cag aac ccc ttt att tgt gac tgc cat ctc aag tgg cta gcg gat tat      1344
Gln Asn Pro Phe Ile Cys Asp Cys His Leu Lys Trp Leu Ala Asp Tyr
                435                 440                 445 ctc cat acc aac ccg att gag acc agt ggt gcc cgt tgc acc agc ccc      1392
Leu His Thr Asn Pro Ile Glu Thr Ser Gly Ala Arg Cys Thr Ser Pro
        450                 455                 460 cgc cgc ctg gca aac aaa aga att gga cag atc aaa agc aag aaa ttc      1440
Arg Arg Leu Ala Asn Lys Arg Ile Gly Gln Ile Lys Ser Lys Lys Phe
465                 470                 475                 480 cgt tgt tca ggt aca gaa gat tat cga tca aaa tta agt gga gac tgc      1488
Arg Cys Ser Gly Thr Glu Asp Tyr Arg Ser Lys Leu Ser Gly Asp Cys
                485                 490                 495 ttt gcg gat ctg gct tgc cct gaa aag tgt cgc tgt gaa gga acc aca      1536
Phe Ala Asp Leu Ala Cys Pro Glu Lys Cys Arg Cys Glu Gly Thr Thr
                500                 505                 510 gta gat tgc tct aat caa aag ctc aac aaa atc ccg gag cac att ccc      1584
Val Asp Cys Ser Asn Gln Lys Leu Asn Lys Ile Pro Glu His Ile Pro
                515                 520                 525 cag tac act gca gag ttg cgt ctc aat aat aat gaa ttt acc gtg ttg      1632
Gln Tyr Thr Ala Glu Leu Arg Leu Asn Asn Asn Glu Phe Thr Val Leu
        530                 535                 540 gaa gcc aca gga atc ttt aag aaa ctt cct caa tta cgt aaa ata aac      1680
Glu Ala Thr Gly Ile Phe Lys Lys Leu Pro Gln Leu Arg Lys Ile Asn
545                 550                 555                 560 ttt agc aac aat aag atc aca gat att gag gag gga gca ttt gaa gga      1728
Phe Ser Asn Asn Lys Ile Thr Asp Ile Glu Glu Gly Ala Phe Glu Gly
                565                 570                 575 gca tct ggt gta aat gaa ata ctt ctt acg agt aat cgt ttg gaa aat      1776
Ala Ser Gly Val Asn Glu Ile Leu Leu Thr Ser Asn Arg Leu Glu Asn
                580                 585                 590 gtg cag cat aag atg ttc aag gga ttg gaa agc ctc aaa act ttg atg      1824
Val Gln His Lys Met Phe Lys Gly Leu Glu Ser Leu Lys Thr Leu Met
                595                 600                 605 ttg aga agc aat cga ata acc tgt gtg ggg aat gac agt ttc ata gga      1872
Leu Arg Ser Asn Arg Ile Thr Cys Val Gly Asn Asp Ser Phe Ile Gly
        610                 615                 620 ctc agt tct gtg cgt ttg ctt tct ttg tat gat aat caa att act aca      1920
Leu Ser Ser Val Arg Leu Leu Ser Leu Tyr Asp Asn Gln Ile Thr Thr
625                 630                 635                 640 gtt gca cca ggg gca ttt gat act ctc cat tct tta tct act cta aac      1968
Val Ala Pro Gly Ala Phe Asp Thr Leu His Ser Leu Ser Thr Leu Asn
                645                 650                 655 ctc ttg gcc aat cct ttt aac tgt aac tgc tac ctg gct tgg ttg gga      2016
Leu Leu Ala Asn Pro Phe Asn Cys Asn Cys Tyr Leu Ala Trp Leu Gly
```

```
                  660             665             670
gag tgg ctg aga aag aag aga att gtc acg gga aat cct aga tgt caa    2064
Glu Trp Leu Arg Lys Lys Arg Ile Val Thr Gly Asn Pro Arg Cys Gln
        675             680             685 aaa cca tac ttc ctg aaa gaa ata ccc atc cag gat gtg gcc att cag    2112
Lys Pro Tyr Phe Leu Lys Glu Ile Pro Ile Gln Asp Val Ala Ile Gln
690             695             700 gac ttc act tgt gat gac gga aat gat gac aat agt tgc tcc cca ctt    2160
Asp Phe Thr Cys Asp Asp Gly Asn Asp Asp Asn Ser Cys Ser Pro Leu
705             710             715             720 tct cgc tgt cct act gaa tgt act tgc ttg gat aca gtc gtc cga tgt    2208
Ser Arg Cys Pro Thr Glu Cys Thr Cys Leu Asp Thr Val Val Arg Cys
            725             730             735 agc aac aag ggt ttg aag gtc ttg ccg aaa ggt att cca aga gat gtc    2256
Ser Asn Lys Gly Leu Lys Val Leu Pro Lys Gly Ile Pro Arg Asp Val
        740             745             750 aca gag ttg tat ctg gat gga aac caa ttt aca ctg gtt ccc aag gaa    2304
Thr Glu Leu Tyr Leu Asp Gly Asn Gln Phe Thr Leu Val Pro Lys Glu
        755             760             765 ctc tcc aac tac aaa cat tta aca ctt ata gac tta agt aac aac aga    2352
Leu Ser Asn Tyr Lys His Leu Thr Leu Ile Asp Leu Ser Asn Asn Arg
770             775             780 ata agc acg ctt tct aat cag agc ttc agc aac atg acc cag ctc ctc    2400
Ile Ser Thr Leu Ser Asn Gln Ser Phe Ser Asn Met Thr Gln Leu Leu
785             790             795             800 acc tta att ctt agt tac aac cgt ctg aga tgt att cct cct cgc acc    2448
Thr Leu Ile Leu Ser Tyr Asn Arg Leu Arg Cys Ile Pro Pro Arg Thr
            805             810             815 ttt gat gga tta aag tct ctt cga tta ctt tct cta cat gga aat gac    2496
Phe Asp Gly Leu Lys Ser Leu Arg Leu Leu Ser Leu His Gly Asn Asp
        820             825             830 att tct gtt gtg cct gaa ggt gct ttc aat gat ctt tct gca tta tca    2544
Ile Ser Val Val Pro Glu Gly Ala Phe Asn Asp Leu Ser Ala Leu Ser
        835             840             845 cat cta gca att gga gcc aac cct ctt tac tgt gat tgt aac atg cag    2592
His Leu Ala Ile Gly Ala Asn Pro Leu Tyr Cys Asp Cys Asn Met Gln
850             855             860 tgg tta tcc gac tgg gtg aag tcg gaa tat aag gag cct gga att gct    2640
Trp Leu Ser Asp Trp Val Lys Ser Glu Tyr Lys Glu Pro Gly Ile Ala
865             870             875             880 cgt tgt gct ggt cct gga gaa atg gca gat aaa ctt tta ctc aca act    2688
Arg Cys Ala Gly Pro Gly Glu Met Ala Asp Lys Leu Leu Leu Thr Thr
            885             890             895 ccc tcc aaa aaa ttt acc tgt caa ggt cct gtg gat gtc aat att cta    2736
Pro Ser Lys Lys Phe Thr Cys Gln Gly Pro Val Asp Val Asn Ile Leu
        900             905             910 gct aag tgt aac ccc tgc cta tca aat ccg tgt aaa aat gat ggc aca    2784
Ala Lys Cys Asn Pro Cys Leu Ser Asn Pro Cys Lys Asn Asp Gly Thr
        915             920             925 tgt aat agt gat cca gtt gac ttt tac cga tgc acc tgt cca tat ggt    2832
Cys Asn Ser Asp Pro Val Asp Phe Tyr Arg Cys Thr Cys Pro Tyr Gly
930             935             940 ttc aag ggg cag gac tgt gat gtc cca att cat gcc tgc atc agt aac    2880
Phe Lys Gly Gln Asp Cys Asp Val Pro Ile His Ala Cys Ile Ser Asn
945             950             955             960 cca tgt aaa cat gga gga act tgc cac tta aag gaa gga gaa gat        2928
Pro Cys Lys His Gly Gly Thr Cys His Leu Lys Glu Gly Glu Glu Asp
            965             970             975 gga ttc tgg tgt att tgt gct gat gga ttt gaa gga gaa aat tgt gaa    2976
```

```
                                                          -continued

Gly Phe Trp Cys Ile Cys Ala Asp Gly Phe Glu Gly Glu Asn Cys Glu
            980                 985                 990 gtc aac gtt gat gat tgt gaa gat aat gac tgt gaa aat aat tct aca       3024
Val Asn Val Asp Asp Cys Glu Asp Asn Asp Cys Glu Asn Asn Ser Thr
            995                 1000                1005 tgt gtc gat ggc att aat aac tac aca tgc ctt tgc cca cct gag tat       3072
Cys Val Asp Gly Ile Asn Asn Tyr Thr Cys Leu Cys Pro Pro Glu Tyr
    1010                1015                1020 aca ggt gag ttg tgt gag gag aag ctg gac ttc tgt gcc cag gac ctg       3120
Thr Gly Glu Leu Cys Glu Glu Lys Leu Asp Phe Cys Ala Gln Asp Leu
1025                1030                1035                1040 aac ccc tgc cag cac gat tca aag tgc atc cta act cca aag gga ttc       3168
Asn Pro Cys Gln His Asp Ser Lys Cys Ile Leu Thr Pro Lys Gly Phe
                1045                1050                1055 aaa tgt gac tgc aca cca ggg tac gta ggt gaa cac tgc gac atc gat       3216
Lys Cys Asp Cys Thr Pro Gly Tyr Val Gly Glu His Cys Asp Ile Asp
            1060                1065                1070 ttt gac gac tgc caa gac aac aag tgt aaa aac gga gcc cac tgc aca       3264
Phe Asp Asp Cys Gln Asp Asn Lys Cys Lys Asn Gly Ala His Cys Thr
        1075                1080                1085 gat gca gtg aac ggc tat acg tgc ata tgc ccc gaa ggt tac agt ggc       3312
Asp Ala Val Asn Gly Tyr Thr Cys Ile Cys Pro Glu Gly Tyr Ser Gly
    1090                1095                1100 ttg ttc tgt gag ttt tct cca ccc atg gtc ctc cct cgt acc agc ccc       3360
Leu Phe Cys Glu Phe Ser Pro Pro Met Val Leu Pro Arg Thr Ser Pro
1105                1110                1115                1120 tgt gat aat ttt gat tgt cag aat gga gct cag tgt atc gtc aga ata       3408
Cys Asp Asn Phe Asp Cys Gln Asn Gly Ala Gln Cys Ile Val Arg Ile
                1125                1130                1135 aat gag cca ata tgt cag tgt ttg cct ggc tat cag gga gaa aag tgt       3456
Asn Glu Pro Ile Cys Gln Cys Leu Pro Gly Tyr Gln Gly Glu Lys Cys
            1140                1145                1150 gaa aaa ttg gtt agt gtg aat ttt ata aac aaa gag tct tat ctt cag       3504
Glu Lys Leu Val Ser Val Asn Phe Ile Asn Lys Glu Ser Tyr Leu Gln
        1155                1160                1165 att cct tca gcc aag gtt cgg cct cag acg aac ata aca ctt cag att       3552
Ile Pro Ser Ala Lys Val Arg Pro Gln Thr Asn Ile Thr Leu Gln Ile
    1170                1175                1180 gcc aca gat gaa gac agc gga atc ctc ctg tat aag ggt gac aaa gac       3600
Ala Thr Asp Glu Asp Ser Gly Ile Leu Leu Tyr Lys Gly Asp Lys Asp
1185                1190                1195                1200 cat atc gcg gta gaa ctc tat cgg ggg cgt gtt cgt gcc agc tat gac       3648
His Ile Ala Val Glu Leu Tyr Arg Gly Arg Val Arg Ala Ser Tyr Asp
                1205                1210                1215 acc ggc tct cat cca gct tct gcc att tac agt gtg gag aca atc aat       3696
Thr Gly Ser His Pro Ala Ser Ala Ile Tyr Ser Val Glu Thr Ile Asn
            1220                1225                1230 gat gga aac ttc cac att gtg gaa cta ctt gcc ttg gat cag agt ctc       3744
Asp Gly Asn Phe His Ile Val Glu Leu Leu Ala Leu Asp Gln Ser Leu
        1235                1240                1245 tct ttg tcc gtg gat ggt ggg aac ccc aaa atc atc act aac ttg tca       3792
Ser Leu Ser Val Asp Gly Gly Asn Pro Lys Ile Ile Thr Asn Leu Ser
    1250                1255                1260 aag cag tcc act ctg aat ttt gac tct cca ctc tat gta gga ggc atg       3840
Lys Gln Ser Thr Leu Asn Phe Asp Ser Pro Leu Tyr Val Gly Gly Met
1265                1270                1275                1280 cca ggg aag agt aac gtg gca tct ctg cgc cag gcc cct ggg cag aac       3888
Pro Gly Lys Ser Asn Val Ala Ser Leu Arg Gln Ala Pro Gly Gln Asn
                1285                1290                1295
```

```
gga acc agc ttc cac ggc tgc atc cgg aac ctt tac atc aac agt gag    3936
Gly Thr Ser Phe His Gly Cys Ile Arg Asn Leu Tyr Ile Asn Ser Glu
        1300                1305                1310 ctg cag gac ttc cag aag gtg ccg atg caa aca ggc att ttg cct ggc    3984
Leu Gln Asp Phe Gln Lys Val Pro Met Gln Thr Gly Ile Leu Pro Gly
    1315                1320                1325 tgt gag cca tgc cac aag aag gtg tgt gcc cat ggc aca tgc cag ccc    4032
Cys Glu Pro Cys His Lys Lys Val Cys Ala His Gly Thr Cys Gln Pro
1330                1335                1340 agc agc cag gca ggc ttc acc tgc gag tgc cag gaa gga tgg atg ggg    4080
Ser Ser Gln Ala Gly Phe Thr Cys Glu Cys Gln Glu Gly Trp Met Gly
        1345                1350                1355                1360 ccc ctc tgt gac caa cgg acc aat gac cct tgc ctt gga aat aaa tgc    4128
Pro Leu Cys Asp Gln Arg Thr Asn Asp Pro Cys Leu Gly Asn Lys Cys
            1365                1370                1375 gta cat ggc acc tgc ttg ccc atc aat gcg ttc tcc tac agc tgt aag    4176
Val His Gly Thr Cys Leu Pro Ile Asn Ala Phe Ser Tyr Ser Cys Lys
        1380                1385                1390 tgc ttg gag ggc cat gga ggt gtc ctc tgt gat gaa gag gag gat ctg    4224
Cys Leu Glu Gly His Gly Gly Val Leu Cys Asp Glu Glu Glu Asp Leu
    1395                1400                1405 ttt aac cca tgc cag gcg atc aag tgc aag cat ggg aag tgc agg ctt    4272
Phe Asn Pro Cys Gln Ala Ile Lys Cys Lys His Gly Lys Cys Arg Leu
1410                1415                1420 tca ggt ctg ggg cag ccc tac tgt gaa tgc agc agt gga tac acg ggg    4320
Ser Gly Leu Gly Gln Pro Tyr Cys Glu Cys Ser Ser Gly Tyr Thr Gly
1425                1430                1435                1440 gac agc tgt gat cga gaa atc tct tgt cga ggg gaa agg ata aga gat    4368
Asp Ser Cys Asp Arg Glu Ile Ser Cys Arg Gly Glu Arg Ile Arg Asp
            1445                1450                1455 tat tac caa aag cag cag ggc tat gct gct tgc caa aca acc aag aag    4416
Tyr Tyr Gln Lys Gln Gln Gly Tyr Ala Ala Cys Gln Thr Thr Lys Lys
        1460                1465                1470 gtg tcc cga tta gag tgc aga ggt ggg tgt gca gga ggg cag tgc tgt    4464
Val Ser Arg Leu Glu Cys Arg Gly Gly Cys Ala Gly Gly Gln Cys Cys
    1475                1480                1485 gga ccg ctg agg agc aag cgg cgg aaa tac tct ttc gaa tgc act gac    4512
Gly Pro Leu Arg Ser Lys Arg Arg Lys Tyr Ser Phe Glu Cys Thr Asp
1490                1495                1500 ggc tcc tcc ttt gtg gac gag gtt gag aaa gtg gtg aag tgc ggc tgt    4560
Gly Ser Ser Phe Val Asp Glu Val Glu Lys Val Val Lys Cys Gly Cys
1505                1510                1515                1520 acg agg tgt gtg tcc taaacacact cccggcagct ctgtctttgg aaaaggttgt    4615
Thr Arg Cys Val Ser
            1525 atacttcttg accatgtggg actaatgaat gcttcatagt ggaaatattt gaaatatatt    4675 gtaaaataca gaacagactt attttttatta tgagaataaa gactttttttt ctgcatttgg    4735 aaaaaaaaaa aaaaaaaact cga                                           4758

<210> SEQ ID NO 2
<211> LENGTH: 1525
<212> TYPE: PRT
<213> ORGANISM: human

<400> SEQUENCE: 2

Met Arg Gly Val Gly Trp Gln Met Leu Ser Leu Ser Leu Gly Leu Val
 1               5                   10                  15

Leu Ala Ile Leu Asn Lys Val Ala Pro Gln Ala Cys Pro Ala Gln Cys
            20                  25                  30
```

```
Ser Cys Ser Gly Ser Thr Val Asp Cys His Gly Leu Ala Leu Arg Ser
         35                  40                  45

Val Pro Arg Asn Ile Pro Arg Asn Thr Glu Arg Leu Asp Leu Asn Gly
 50                  55                  60

Asn Asn Ile Thr Arg Ile Thr Lys Thr Asp Phe Ala Gly Leu Arg His
 65                  70                  75                  80

Leu Arg Val Leu Gln Leu Met Glu Asn Lys Ile Ser Thr Ile Glu Arg
                 85                  90                  95

Gly Ala Phe Gln Asp Leu Lys Glu Leu Glu Arg Leu Arg Leu Asn Arg
                100                 105                 110

Asn His Leu Gln Leu Phe Pro Glu Leu Leu Phe Leu Gly Thr Ala Lys
            115                 120                 125

Leu Tyr Arg Leu Asp Leu Ser Glu Asn Gln Ile Gln Ala Ile Pro Arg
130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
                180                 185                 190

Ala Ser Phe Asn His Met Pro Lys Leu Arg Thr Phe Arg Leu His Ser
            195                 200                 205

Asn Asn Leu Tyr Cys Asp Cys His Leu Ala Trp Leu Ser Asp Trp Leu
            210                 215                 220

Arg Lys Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Gly His Gln Ser Phe Met Ala Pro Ser Cys
                260                 265                 270

Ser Val Leu His Cys Pro Ala Ala Cys Thr Cys Ser Asn Asn Ile Val
            275                 280                 285

Asp Cys Arg Gly Lys Gly Leu Thr Glu Ile Pro Thr Asn Leu Pro Glu
290                 295                 300

Thr Ile Thr Glu Ile Arg Leu Glu Gln Asn Thr Ile Lys Val Ile Pro
305                 310                 315                 320

Pro Gly Ala Phe Ser Pro Tyr Lys Lys Leu Arg Arg Ile Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
            355                 360                 365

Lys Ser Leu Phe Glu Gly Leu Phe Ser Leu Gln Leu Leu Leu Leu Asn
            370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Ile Ala
                405                 410                 415

Lys Gly Thr Phe Ser Pro Leu Arg Ala Ile Gln Thr Met His Leu Ala
                420                 425                 430

Gln Asn Pro Phe Ile Cys Asp Cys His Leu Lys Trp Leu Ala Asp Tyr
            435                 440                 445
```

```
Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Phe
465                 470                 475                 480

Arg Cys Ser Gly Thr Glu Asp Tyr Arg Ser Lys Leu Ser Gly Asp Cys
                    485                 490                 495

Phe Ala Asp Leu Ala Cys Pro Glu Lys Cys Arg Cys Glu Gly Thr Thr
                500                 505                 510

Val Asp Cys Ser Asn Gln Lys Leu Asn Lys Ile Pro Glu His Ile Pro
                515                 520                 525

Gln Tyr Thr Ala Glu Leu Arg Leu Asn Asn Glu Phe Thr Val Leu
                530                 535                 540

Glu Ala Thr Gly Ile Phe Lys Lys Leu Pro Gln Leu Arg Lys Ile Asn
545                 550                 555                 560

Phe Ser Asn Asn Lys Ile Thr Asp Ile Glu Glu Gly Ala Phe Glu Gly
                    565                 570                 575

Ala Ser Gly Val Asn Glu Ile Leu Leu Thr Ser Asn Arg Leu Glu Asn
                580                 585                 590

Val Gln His Lys Met Phe Lys Gly Leu Glu Ser Leu Lys Thr Leu Met
                595                 600                 605

Leu Arg Ser Asn Arg Ile Thr Cys Val Gly Asn Asp Ser Phe Ile Gly
    610                 615                 620

Leu Ser Ser Val Arg Leu Leu Ser Leu Tyr Asp Asn Gln Ile Thr Thr
625                 630                 635                 640

Val Ala Pro Gly Ala Phe Asp Thr Leu His Ser Leu Ser Thr Leu Asn
                    645                 650                 655

Leu Leu Ala Asn Pro Phe Asn Cys Asn Cys Tyr Leu Ala Trp Leu Gly
                    660                 665                 670

Glu Trp Leu Arg Lys Lys Arg Ile Val Thr Gly Asn Pro Arg Cys Gln
    675                 680                 685

Lys Pro Tyr Phe Leu Lys Glu Ile Pro Ile Gln Asp Val Ala Ile Gln
    690                 695                 700

Asp Phe Thr Cys Asp Asp Gly Asn Asp Asp Asn Ser Cys Ser Pro Leu
705                 710                 715                 720

Ser Arg Cys Pro Thr Glu Cys Thr Cys Leu Asp Thr Val Val Arg Cys
                    725                 730                 735

Ser Asn Lys Gly Leu Lys Val Leu Pro Lys Gly Ile Pro Arg Asp Val
                740                 745                 750

Thr Glu Leu Tyr Leu Asp Gly Asn Gln Phe Thr Leu Val Pro Lys Glu
                755                 760                 765

Leu Ser Asn Tyr Lys His Leu Thr Leu Ile Asp Leu Ser Asn Asn Arg
    770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                805                 810                 815

Phe Asp Gly Leu Lys Ser Leu Arg Leu Leu Ser Leu His Gly Asn Asp
                820                 825                 830

Ile Ser Val Val Pro Glu Gly Ala Phe Asn Asp Leu Ser Ala Leu Ser
                835                 840                 845

His Leu Ala Ile Gly Ala Asn Pro Leu Tyr Cys Asp Cys Asn Met Gln
    850                 855                 860

Trp Leu Ser Asp Trp Val Lys Ser Glu Tyr Lys Glu Pro Gly Ile Ala
```

```
865                 870                 875                 880
Arg Cys Ala Gly Pro Gly Glu Met Ala Asp Lys Leu Leu Leu Thr Thr
                885                 890                 895
Pro Ser Lys Lys Phe Thr Cys Gln Gly Pro Val Asp Val Asn Ile Leu
            900                 905                 910
Ala Lys Cys Asn Pro Cys Leu Ser Asn Pro Cys Lys Asn Asp Gly Thr
        915                 920                 925
Cys Asn Ser Asp Pro Val Asp Phe Tyr Arg Cys Thr Cys Pro Tyr Gly
    930                 935                 940
Phe Lys Gly Gln Asp Cys Asp Val Pro Ile His Ala Cys Ile Ser Asn
945                 950                 955                 960
Pro Cys Lys His Gly Gly Thr Cys His Leu Lys Glu Gly Glu Glu Asp
                965                 970                 975
Gly Phe Trp Cys Ile Cys Ala Asp Gly Phe Glu Gly Glu Asn Cys Glu
            980                 985                 990
Val Asn Val Asp Asp Cys Glu Asp Asn Asp Cys Glu Asn Asn Ser Thr
        995                 1000                1005
Cys Val Asp Gly Ile Asn Asn Tyr Thr Cys Leu Cys Pro Pro Glu Tyr
    1010                1015                1020
Thr Gly Glu Leu Cys Glu Glu Lys Leu Asp Phe Cys Ala Gln Asp Leu
1025                1030                1035                1040
Asn Pro Cys Gln His Asp Ser Lys Cys Ile Leu Thr Pro Lys Gly Phe
                1045                1050                1055
Lys Cys Asp Cys Thr Pro Gly Tyr Val Gly Glu His Cys Asp Ile Asp
            1060                1065                1070
Phe Asp Asp Cys Gln Asp Asn Lys Cys Lys Asn Gly Ala His Cys Thr
        1075                1080                1085
Asp Ala Val Asn Gly Tyr Thr Cys Ile Cys Pro Glu Gly Tyr Ser Gly
    1090                1095                1100
Leu Phe Cys Glu Phe Ser Pro Pro Met Val Leu Pro Arg Thr Ser Pro
1105                1110                1115                1120
Cys Asp Asn Phe Asp Cys Gln Asn Gly Ala Gln Cys Ile Val Arg Ile
                1125                1130                1135
Asn Glu Pro Ile Cys Gln Cys Leu Pro Gly Tyr Gln Gly Glu Lys Cys
            1140                1145                1150
Glu Lys Leu Val Ser Val Asn Phe Ile Asn Lys Glu Ser Tyr Leu Gln
        1155                1160                1165
Ile Pro Ser Ala Lys Val Arg Pro Gln Thr Asn Ile Thr Leu Gln Ile
    1170                1175                1180
Ala Thr Asp Glu Asp Ser Gly Ile Leu Leu Tyr Lys Gly Asp Lys Asp
1185                1190                1195                1200
His Ile Ala Val Glu Leu Tyr Arg Gly Arg Val Arg Ala Ser Tyr Asp
                1205                1210                1215
Thr Gly Ser His Pro Ala Ser Ala Ile Tyr Ser Val Glu Thr Ile Asn
            1220                1225                1230
Asp Gly Asn Phe His Ile Val Glu Leu Leu Ala Leu Asp Gln Ser Leu
        1235                1240                1245
Ser Leu Ser Val Asp Gly Gly Asn Pro Lys Ile Ile Thr Asn Leu Ser
    1250                1255                1260
Lys Gln Ser Thr Leu Asn Phe Asp Ser Pro Leu Tyr Val Gly Gly Met
1265                1270                1275                1280
Pro Gly Lys Ser Asn Val Ala Ser Leu Arg Gln Ala Pro Gly Gln Asn
                1285                1290                1295
```

```
Gly Thr Ser Phe His Gly Cys Ile Arg Asn Leu Tyr Ile Asn Ser Glu
            1300                1305                1310
Leu Gln Asp Phe Gln Lys Val Pro Met Gln Thr Gly Ile Leu Pro Gly
        1315                1320                1325
Cys Glu Pro Cys His Lys Lys Val Cys Ala His Gly Thr Cys Gln Pro
    1330                1335                1340
Ser Ser Gln Ala Gly Phe Thr Cys Glu Cys Gln Glu Gly Trp Met Gly
1345                1350                1355                1360
Pro Leu Cys Asp Gln Arg Thr Asn Asp Pro Cys Leu Gly Asn Lys Cys
            1365                1370                1375
Val His Gly Thr Cys Leu Pro Ile Asn Ala Phe Ser Tyr Ser Cys Lys
        1380                1385                1390
Cys Leu Glu Gly His Gly Gly Val Leu Cys Asp Glu Glu Asp Leu
    1395                1400                1405
Phe Asn Pro Cys Gln Ala Ile Lys Cys Lys His Gly Lys Cys Arg Leu
    1410                1415                1420
Ser Gly Leu Gly Gln Pro Tyr Cys Glu Cys Ser Ser Gly Tyr Thr Gly
1425                1430                1435                1440
Asp Ser Cys Asp Arg Glu Ile Ser Cys Arg Gly Glu Arg Ile Arg Asp
            1445                1450                1455
Tyr Tyr Gln Lys Gln Gly Tyr Ala Ala Cys Gln Thr Thr Lys Lys
        1460                1465                1470
Val Ser Arg Leu Glu Cys Arg Gly Gly Cys Ala Gly Gly Gln Cys Cys
            1475                1480                1485
Gly Pro Leu Arg Ser Lys Arg Arg Lys Tyr Ser Phe Glu Cys Thr Asp
        1490                1495                1500
Gly Ser Ser Phe Val Asp Glu Val Glu Lys Val Val Lys Cys Gly Cys
1505                1510                1515                1520
Thr Arg Cys Val Ser
            1525

<210> SEQ ID NO 3
<211> LENGTH: 105
<212> TYPE: PRT
<213> ORGANISM: human

<400> SEQUENCE: 3

Ser Pro Cys Thr Cys Ser Asn Asn Ile Val Asp Cys Arg Gly Lys Gly
1               5                   10                  15
Leu Met Glu Ile Pro Ala Asn Leu Pro Glu Gly Ile Val Glu Ile Arg
            20                  25                  30
Leu Glu Gln Asn Ser Ile Lys Ala Ile Pro Ala Gly Ala Phe Thr Gln
        35                  40                  45
Tyr Lys Lys Leu Lys Arg Ile Asp Ile Ser Lys Asn Gln Ile Ser Asp
    50                  55                  60
Ile Ala Pro Asp Ala Phe Gln Gly Leu Lys Ser Leu Thr Ser Leu Val
65                  70                  75                  80
Leu Tyr Gly Asn Lys Ile Thr Glu Ile Ala Lys Gly Leu Phe Asp Gly
                85                  90                  95
Leu Val Ser Leu Gln Leu Leu Leu
            100                 105

<210> SEQ ID NO 4
<211> LENGTH: 138
<212> TYPE: PRT
```

```
<213> ORGANISM: human

<400> SEQUENCE: 4

Glu Gly Ala Phe Asn Gly Ala Ala Ser Val Gln Glu Leu Met Leu Thr
 1               5                  10                  15

Gly Asn Gln Leu Glu Thr Val His Gly Arg Gly Phe Arg Gly Gly Leu
                20                  25                  30

Ser Gly Leu Lys Thr Leu Met Leu Arg Ser Asn Leu Ile Gly Cys Val
            35                  40                  45

Ser Asn Asp Thr Phe Ala Gly Leu Ser Ser Val Arg Leu Leu Ser Leu
        50                  55                  60

Tyr Asp Asn Arg Ile Thr Thr Ile Thr Pro Gly Ala Phe Thr Thr Leu
 65                  70                  75                  80

Val Ser Leu Ser Thr Ile Asn Leu Leu Ser Asn Pro Phe Asn Cys Asn
                85                  90                  95

Cys His Leu Gly Ala Gly Leu Gly Lys Trp Leu Arg Lys Arg Arg Ile
                100                 105                 110

Val Ser Gly Asn Pro Arg Cys Gln Lys Pro Phe Phe Leu Lys Glu Ile
            115                 120                 125

Pro Ile Gln Gly Val Gly His Pro Gly Ile
        130                 135

<210> SEQ ID NO 5
<211> LENGTH: 160
<212> TYPE: PRT
<213> ORGANISM: human

<400> SEQUENCE: 5

Trp Pro Arg Cys Glu Cys Met Pro Gly Tyr Ala Gly Asp Asn Cys Ser
 1               5                  10                  15

Glu Asn Gln Asp Asp Cys Arg Asp His Arg Cys Gln Asn Gly Ala Gln
                20                  25                  30

Cys Met Asp Glu Val Asn Ser Tyr Ser Cys Leu Cys Ala Glu Gly Tyr
            35                  40                  45

Ser Gly Gln Leu Cys Glu Ile Pro Pro His Leu Pro Ala Pro Lys Ser
        50                  55                  60

Pro Cys Glu Gly Thr Glu Cys Gln Asn Gly Ala Asn Cys Val Asp Gln
 65                  70                  75                  80

Gly Asn Arg Pro Val Cys Gln Cys Leu Pro Gly Phe Gly Gly Pro Glu
                85                  90                  95

Cys Glu Lys Leu Leu Ser Val Asn Phe Val Asp Arg Asp Thr Tyr Leu
                100                 105                 110

Gln Phe Thr Asp Leu Gln Asn Trp Xaa Arg Xaa Asn Ile Thr Leu Gln
            115                 120                 125

Val Phe Thr Ala Glu Asp Asn Gly Ile Leu Leu Tyr Asn Gly Gly Asn
        130                 135                 140

Asp His Ile Ala Val Xaa Leu Tyr Xaa Gly His Val Arg Phe Ser Tyr
145                 150                 155                 160

<210> SEQ ID NO 6
<211> LENGTH: 103
<212> TYPE: PRT
<213> ORGANISM: human

<400> SEQUENCE: 6

Gln Cys His Ile Ser Asp Gln Gly Glu Pro Tyr Cys Leu Cys Gln Pro
 1               5                  10                  15
```

```
Gly Phe Ser Gly Glu His Cys Gln Gln Glu Asn Pro Cys Leu Gly Gln
                20                  25                  30

Val Val Arg Glu Val Ile Arg Arg Gln Lys Gly Tyr Ala Ser Cys Ala
        35                  40                  45

Thr Ala Ser Lys Val Pro Ile Met Glu Cys Arg Gly Cys Gly Pro
    50                  55                  60

Gln Cys Cys Gln Pro Thr Arg Ser Lys Arg Arg Lys Tyr Val Phe Gln
65                  70                  75                  80

Cys Thr Asp Gly Ser Ser Phe Val Glu Glu Val Glu Arg His Leu Glu
                85                  90                  95

Cys Gly Cys Leu Ala Cys Ser
            100

<210> SEQ ID NO 7
<211> LENGTH: 1480
<212> TYPE: PRT
<213> ORGANISM: Drosophila melanogaster

<400> SEQUENCE: 7

Met Ala Ala Pro Ser Arg Thr Thr Leu Met Pro Pro Phe Arg Leu
1               5                   10                  15

Gln Leu Arg Leu Leu Ile Leu Pro Ile Leu Leu Leu Arg His Asp
                20                  25                  30

Ala Val His Ala Glu Pro Tyr Ser Gly Gly Phe Gly Ser Ser Ala Val
        35                  40                  45

Ser Ser Gly Gly Leu Gly Ser Val Gly Ile His Ile Pro Gly Gly Gly
    50                  55                  60

Val Gly Val Ile Thr Glu Ala Arg Cys Pro Arg Val Cys Ser Cys Thr
65                  70                  75                  80

Gly Leu Asn Val Asp Cys Ser His Arg Gly Leu Thr Ser Val Pro Arg
                85                  90                  95

Lys Ile Ser Ala Asp Val Glu Arg Leu Glu Leu Gln Gly Asn Asn Leu
                100                 105                 110

Thr Val Ile Tyr Glu Thr Asp Phe Gln Arg Leu Thr Lys Leu Arg Met
            115                 120                 125

Leu Gln Leu Thr Asp Asn Gln Ile His Thr Ile Glu Arg Asn Ser Phe
    130                 135                 140

Gln Asp Leu Val Ser Leu Glu Arg Leu Asp Ile Ser Asn Asn Val Ile
145                 150                 155                 160

Thr Thr Val Gly Arg Arg Val Phe Lys Gly Ala Gln Ser Leu Arg Ser
                165                 170                 175

Leu Gln Leu Asp Asn Asn Gln Ile Thr Cys Leu Asp Glu His Ala Phe
            180                 185                 190

Lys Gly Leu Val Glu Leu Glu Ile Leu Thr Leu Asn Asn Asn Asn Leu
    195                 200                 205

Thr Ser Leu Pro His Asn Ile Phe Gly Gly Leu Gly Arg Leu Arg Ala
    210                 215                 220

Leu Arg Leu Ser Asp Asn Pro Phe Ala Cys Asp Cys His Leu Ser Trp
225                 230                 235                 240

Leu Ser Arg Phe Leu Arg Ser Ala Thr Arg Leu Ala Pro Tyr Thr Arg
                245                 250                 255

Cys Gln Ser Pro Ser Gln Leu Lys Gly Gln Asn Val Ala Asp Leu His
            260                 265                 270

Asp Gln Glu Phe Lys Cys Ser Gly Leu Thr Glu His Ala Pro Met Glu
```

-continued

```
                275                 280                 285
Cys Gly Ala Glu Asn Ser Cys Pro His Pro Cys Arg Cys Ala Asp Gly
    290                 295                 300
Ile Val Asp Cys Arg Glu Lys Ser Leu Thr Ser Val Pro Val Thr Leu
305                 310                 315                 320
Pro Asp Asp Thr Thr Asp Val Arg Leu Glu Gln Asn Phe Ile Thr Glu
                325                 330                 335
Leu Pro Pro Lys Ser Phe Ser Phe Arg Arg Leu Arg Arg Ile Asp
            340                 345                 350
Leu Ser Asn Asn Ile Ser Arg Ile Ala His Asp Ala Leu Ser Gly
        355                 360                 365
Leu Lys Gln Leu Thr Thr Leu Val Leu Tyr Gly Asn Lys Ile Lys Asp
    370                 375                 380
Leu Pro Ser Gly Val Phe Lys Gly Leu Gly Ser Leu Arg Leu Leu
385                 390                 395                 400
Leu Asn Ala Asn Glu Ile Ser Cys Ile Arg Lys Asp Ala Phe Arg Asp
                405                 410                 415
Leu His Ser Leu Ser Leu Leu Ser Leu Tyr Asp Asn Asn Ile Gln Ser
            420                 425                 430
Leu Ala Asn Gly Thr Phe Asp Ala Met Lys Ser Met Lys Thr Val His
        435                 440                 445
Leu Ala Lys Asn Pro Phe Ile Cys Asp Cys Asn Leu Arg Trp Leu Ala
    450                 455                 460
Asp Tyr Leu His Lys Asn Pro Ile Glu Thr Ser Gly Ala Arg Cys Glu
465                 470                 475                 480
Ser Pro Lys Arg Met His Arg Arg Ile Glu Ser Leu Arg Glu Glu
                485                 490                 495
Lys Phe Lys Cys Ser Trp Gly Glu Leu Arg Met Lys Leu Ser Gly Glu
            500                 505                 510
Cys Arg Met Asp Ser Asp Cys Pro Ala Met Cys His Cys Glu Gly Thr
        515                 520                 525
Thr Val Asp Cys Thr Gly Arg Arg Leu Lys Glu Ile Pro Arg Asp Ile
    530                 535                 540
Pro Leu His Thr Thr Glu Leu Leu Leu Asn Asp Asn Glu Leu Gly Arg
545                 550                 555                 560
Ile Ser Ser Asp Gly Leu Phe Gly Arg Leu Pro His Leu Val Lys Leu
                565                 570                 575
Glu Leu Lys Arg Asn Gln Leu Thr Gly Ile Glu Pro Asn Ala Phe Glu
            580                 585                 590
Gly Ala Ser His Ile Gln Glu Leu Gln Leu Gly Glu Asn Lys Ile Lys
        595                 600                 605
Glu Ile Ser Asn Lys Met Phe Leu Gly Leu His Gln Leu Lys Thr Leu
    610                 615                 620
Asn Leu Tyr Asp Asn Gln Ile Ser Cys Val Met Pro Gly Ser Phe Glu
625                 630                 635                 640
His Leu Asn Ser Leu Thr Ser Leu Asn Leu Ala Ser Asn Pro Phe Asn
                645                 650                 655
Cys Asn Cys His Leu Ala Trp Phe Ala Glu Cys Val Arg Lys Lys Ser
            660                 665                 670
Leu Asn Gly Gly Ala Ala Arg Cys Gly Ala Pro Ser Lys Val Arg Asp
        675                 680                 685
Val Gln Ile Lys Asp Leu Pro His Ser Glu Phe Lys Cys Ser Ser Glu
    690                 695                 700
```

-continued

```
Asn Ser Glu Gly Cys Leu Gly Asp Gly Tyr Cys Pro Pro Ser Cys Thr
705                 710                 715                 720

Cys Thr Gly Thr Val Val Ala Cys Ser Arg Asn Gln Leu Lys Glu Ile
                725                 730                 735

Pro Arg Gly Ile Pro Ala Glu Thr Ser Glu Leu Tyr Leu Glu Ser Asn
            740                 745                 750

Glu Ile Glu Gln Ile His Tyr Glu Arg Ile Arg His Leu Arg Ser Leu
        755                 760                 765

Thr Arg Leu Asp Leu Ser Asn Asn Gln Ile Thr Ile Leu Ser Asn Tyr
770                 775                 780

Thr Phe Ala Asn Leu Thr Lys Leu Ser Thr Leu Ile Ile Ser Tyr Asn
785                 790                 795                 800

Lys Leu Gln Cys Leu Gln Arg His Ala Leu Ser Gly Leu Asn Asn Leu
                805                 810                 815

Arg Val Val Ser Leu His Gly Asn Arg Ile Ser Met Leu Pro Glu Gly
            820                 825                 830

Ser Phe Glu Asp Leu Lys Ser Leu Thr His Ile Ala Leu Gly Ser Asn
        835                 840                 845

Pro Leu Tyr Cys Asp Cys Gly Leu Lys Trp Phe Ser Asp Trp Ile Lys
850                 855                 860

Leu Asp Tyr Val Glu Pro Gly Ile Ala Arg Cys Ala Glu Pro Glu Gln
865                 870                 875                 880

Met Lys Asp Lys Leu Ile Leu Ser Thr Pro Ser Ser Phe Val Cys
                885                 890                 895

Arg Gly Arg Val Arg Asn Asp Ile Leu Ala Lys Cys Asn Ala Cys Phe
            900                 905                 910

Glu Gln Pro Cys Gln Asn Gln Ala Gln Cys Val Ala Leu Pro Gln Arg
        915                 920                 925

Glu Tyr Gln Cys Leu Cys Gln Pro Gly Tyr His Gly Lys His Cys Glu
        930                 935                 940

Phe Met Ile Asp Ala Cys Tyr Gly Asn Pro Cys Arg Asn Asn Ala Thr
945                 950                 955                 960

Cys Thr Val Leu Glu Glu Gly Arg Phe Ser Cys Gln Cys Ala Pro Gly
                965                 970                 975

Tyr Thr Gly Ala Arg Cys Glu Thr Asn Ile Asp Asp Cys Leu Gly Glu
            980                 985                 990

Ile Lys Cys Gln Asn Asn Ala Thr Cys Ile Asp Gly Val Glu Ser Tyr
        995                 1000                1005

Lys Cys Glu Cys Gln Pro Gly Phe Ser Gly Glu Phe Cys Asp Thr Lys
    1010                1015                1020

Ile Gln Phe Cys Ser Pro Glu Phe Asn Pro Cys Ala Asn Gly Ala Lys
1025                1030                1035                1040

Cys Met Asp His Phe Thr His Tyr Ser Cys Asp Cys Gln Ala Gly Phe
                1045                1050                1055

His Gly Thr Asn Cys Thr Asp Asn Ile Asp Asp Cys Gln Asn His Met
            1060                1065                1070

Cys Gln Asn Gly Gly Thr Cys Val Asp Gly Ile Asn Asp Tyr Gln Cys
        1075                1080                1085

Arg Cys Pro Asp Asp Tyr Thr Gly Lys Tyr Cys Glu Gly His Asn Met
    1090                1095                1100

Ile Ser Met Met Tyr Pro Gln Thr Ser Pro Cys Gln Asn His Glu Cys
1105                1110                1115                1120
```

-continued

Lys His Gly Val Cys Phe Gln Pro Asn Ala Gln Gly Ser Asp Tyr Leu
             1125                1130                1135

Cys Arg Cys His Pro Gly Tyr Thr Gly Lys Trp Cys Glu Tyr Leu Thr
         1140                1145                1150

Ser Ile Ser Phe Val His Asn Asn Ser Phe Val Glu Leu Glu Pro Leu
         1155                1160                1165

Arg Thr Arg Pro Glu Ala Asn Val Thr Ile Val Phe Ser Ser Ala Glu
     1170                1175                1180

Gln Asn Gly Ile Leu Met Tyr Asp Gly Gln Asp Ala His Leu Ala Val
1185                1190                1195                1200

Glu Leu Phe Asn Gly Arg Ile Arg Val Ser Tyr Asp Val Gly Asn His
             1205                1210                1215

Pro Val Ser Thr Met Tyr Ser Phe Glu Met Val Ala Asp Gly Lys Tyr
         1220                1225                1230

His Ala Val Glu Leu Leu Ala Ile Lys Lys Asn Phe Thr Leu Arg Val
         1235                1240                1245

Asp Arg Gly Leu Ala Arg Ser Ile Ile Asn Glu Gly Ser Asn Asp Tyr
     1250                1255                1260

Leu Lys Leu Thr Thr Pro Met Phe Leu Gly Gly Leu Pro Val Asp Pro
1265                1270                1275                1280

Ala Gln Gln Ala Tyr Lys Asn Trp Gln Ile Arg Asn Leu Thr Ser Phe
             1285                1290                1295

Lys Gly Cys Met Lys Glu Val Trp Ile Asn His Lys Leu Val Asp Phe
         1300                1305                1310

Gly Asn Ala Gln Arg Gln Gln Lys Ile Thr Pro Gly Cys Ala Leu Leu
         1315                1320                1325

Glu Gly Glu Gln Gln Glu Glu Glu Asp Asp Glu Gln Asp Phe Met Asp
     1330                1335                1340

Glu Thr Pro His Ile Lys Glu Glu Pro Val Asp Pro Cys Leu Glu Asn
1345                1350                1355                1360

Lys Cys Arg Arg Gly Ser Arg Cys Val Pro Asn Ser Asn Ala Arg Asp
             1365                1370                1375

Gly Tyr Gln Cys Lys Cys Lys His Gly Gln Arg Gly Arg Tyr Cys Asp
         1380                1385                1390

Gln Gly Glu Gly Ser Thr Glu Pro Pro Thr Val Thr Ala Ala Ser Thr
         1395                1400                1405

Cys Arg Lys Glu Gln Val Arg Glu Tyr Tyr Thr Glu Asn Asp Cys Arg
     1410                1415                1420

Ser Arg Gln Pro Leu Lys Tyr Ala Lys Cys Val Gly Gly Cys Gly Asn
1425                1430                1435                1440

Gln Cys Cys Ala Ala Lys Ile Val Arg Arg Arg Lys Val Arg Met Val
             1445                1450                1455

Cys Ser Asn Asn Arg Lys Tyr Ile Lys Asn Leu Asp Ile Val Arg Lys
         1460                1465                1470

Cys Gly Cys Thr Lys Lys Cys Tyr
         1475                1480

<210> SEQ ID NO 8
<211> LENGTH: 155
<212> TYPE: PRT
<213> ORGANISM: Caenorhabditis elegans

<400> SEQUENCE: 8

Arg Asn Pro Xaa Ile Cys Asp Cys Asn Leu Gln Trp Leu Ala Gln Ile
 1               5                  10                  15

```
Asn Leu Gln Lys Asn Ile Glu Thr Ser Gly Ala Arg Cys Glu Gln Pro
             20                  25                  30

Lys Arg Leu Arg Lys Lys Lys Phe Ala Thr Leu Pro Pro Asn Lys Phe
         35                  40                  45

Lys Cys Lys Gly Ser Glu Ser Phe Val Ser Met Tyr Ala Asp Ser Cys
     50                  55                  60

Phe Ile Asp Ser Ile Cys Pro Thr Gln Cys Asp Cys Tyr Gly Thr Thr
 65                  70                  75                  80

Val Asp Cys Asn Lys Arg Gly Leu Asn Thr Ile Pro Thr Ser Ile Pro
                 85                  90                  95

Arg Phe Ala Thr Gln Leu Leu Leu Ser Gly Asn Asn Ile Ser Thr Val
            100                 105                 110

Asp Leu Asn Ser Asn Ile His Val Leu Glu Asn Leu Glu Xaa Leu Asp
            115                 120                 125

Leu Ser Asn Asn His Ile Thr Phe Ile Asn Asp Lys Ser Phe Glu Lys
            130                 135                 140

Leu Ser Lys Leu Arg Glu Leu Xaa Leu Asn Asp
145                 150                 155

<210> SEQ ID NO 9
<211> LENGTH: 735
<212> TYPE: PRT
<213> ORGANISM: Caenorhabditis elegans

<400> SEQUENCE: 9

Ser Asn Lys Asn Leu Thr Ser Phe Pro Ser Arg Ile Pro Phe Asp Thr
 1               5                  10                  15

Thr Glu Leu Tyr Leu Asp Ala Asn Tyr Ile Asn Glu Ile Pro Ala His
             20                  25                  30

Asp Leu Asn Arg Leu Tyr Ser Leu Thr Lys Leu Asp Leu Ser His Asn
         35                  40                  45

Arg Leu Ile Ser Leu Glu Asn Asn Thr Phe Ser Asn Leu Thr Arg Leu
     50                  55                  60

Ser Thr Leu Ile Ile Ser Tyr Asn Lys Leu Arg Cys Leu Gln Pro Leu
 65                  70                  75                  80

Ala Phe Asn Gly Leu Asn Ala Leu Arg Ile Leu Ser Leu His Gly Asn
                 85                  90                  95

Asp Ile Ser Phe Leu Pro Gln Ser Ala Phe Ser Asn Leu Thr Ser Ile
            100                 105                 110

Thr His Ile Ala Val Gly Ser Asn Ser Leu Tyr Cys Asp Cys Asn Met
            115                 120                 125

Ala Trp Phe Ser Lys Trp Ile Lys Ser Lys Phe Ile Glu Ala Gly Ile
            130                 135                 140

Ala Arg Cys Glu Tyr Pro Asn Thr Val Ser Asn Gln Leu Leu Leu Thr
145                 150                 155                 160

Ala Gln Pro Tyr Gln Phe Thr Cys Asp Ser Lys Val Pro Thr Lys Leu
            165                 170                 175

Ala Thr Lys Cys Asp Leu Cys Leu Asn Ser Pro Cys Lys Asn Asn Ala
            180                 185                 190

Ile Cys Glu Thr Thr Ser Ser Arg Lys Tyr Thr Cys Asn Cys Thr Pro
            195                 200                 205

Gly Phe Tyr Gly Val His Cys Glu Asn Gln Ile Asp Ala Cys Tyr Gly
            210                 215                 220

Ser Pro Cys Leu Asn Asn Ala Thr Cys Lys Val Ala Gln Ala Gly Arg
```

-continued

```
                225                 230                 235                 240
        Phe Asn Cys Tyr Cys Asn Lys Gly Phe Glu Gly Asp Tyr Cys Glu Lys
                        245                 250                 255
        Asn Ile Asp Asp Cys Val Asn Ser Lys Cys Glu Asn Gly Gly Lys Cys
                        260                 265                 270
        Val Asp Leu Val Arg Phe Cys Ser Glu Glu Leu Lys Asn Phe Gln Ser
                        275                 280                 285
        Phe Gln Ile Asn Ser Tyr Arg Cys Asp Cys Pro Met Glu Tyr Glu Gly
                        290                 295                 300
        Lys His Cys Glu Asp Lys Leu Glu Tyr Cys Thr Lys Lys Leu Asn Pro
        305                 310                 315                 320
        Cys Glu Asn Asn Gly Lys Cys Ile Pro Ile Asn Gly Ser Tyr Ser Cys
                        325                 330                 335
        Met Cys Ser Pro Gly Phe Thr Gly Asn Asn Cys Glu Thr Asn Ile Asp
                        340                 345                 350
        Asp Cys Lys Asn Val Glu Cys Gln Asn Gly Gly Ser Cys Val Asp Gly
                        355                 360                 365
        Ile Leu Ser Tyr Asp Cys Leu Cys Arg Pro Gly Tyr Ala Gly Gln Tyr
                370                 375                 380
        Cys Glu Ile Pro Pro Met Met Asp Met Glu Tyr Gln Lys Thr Asp Ala
        385                 390                 395                 400
        Cys Gln Gln Ser Ala Cys Gly Gln Gly Glu Cys Val Ala Ser Gln Asn
                        405                 410                 415
        Ser Ser Asp Phe Thr Cys Lys Cys His Glu Gly Phe Ser Gly Pro Ser
                        420                 425                 430
        Cys Asp Arg Gln Met Ser Val Gly Phe Lys Asn Pro Gly Ala Tyr Leu
                        435                 440                 445
        Ala Leu Asp Pro Leu Ala Ser Asp Gly Thr Ile Thr Met Thr Leu Arg
                450                 455                 460
        Thr Thr Ser Lys Ile Gly Ile Leu Leu Tyr Tyr Gly Asp Asp His Phe
        465                 470                 475                 480
        Val Ser Ala Glu Leu Tyr Asp Gly Arg Val Lys Leu Val Tyr Tyr Ile
                        485                 490                 495
        Gly Asn Phe Pro Ala Ser His Met Tyr Ser Ser Val Lys Val Asn Asp
                        500                 505                 510
        Gly Leu Pro His Arg Ile Ser Ile Arg Thr Ser Glu Arg Lys Cys Phe
                        515                 520                 525
        Leu Gln Ile Asp Lys Asn Pro Val Gln Ile Val Glu Asn Ser Gly Lys
                530                 535                 540
        Ser Asp Gln Leu Ile Thr Lys Gly Lys Glu Met Leu Tyr Ile Gly Gly
        545                 550                 555                 560
        Leu Pro Ile Glu Lys Ser Gln Asp Ala Lys Arg Arg Phe His Val Lys
                        565                 570                 575
        Asn Ser Glu Ser Leu Lys Gly Cys Ile Ser Ser Ile Thr Ile Asn Glu
                        580                 585                 590
        Val Pro Ile Asn Leu Gln Gln Ala Leu Glu Asn Val Asn Thr Glu Gln
                        595                 600                 605
        Ser Cys Ser Ala Thr Val Asn Phe Cys Ala Gly Ile Asp Cys Gly Asn
                        610                 615                 620
        Gly Lys Cys Thr Asn Asn Ala Leu Ser Pro Lys Gly Tyr Met Cys Gln
        625                 630                 635                 640
        Cys Asp Ser His Phe Ser Gly Glu His Cys Asp Glu Lys Arg Ile Lys
                        645                 650                 655
```

```
Cys Asp Lys Gln Lys Phe Arg Arg His His Ile Glu Asn Glu Cys Arg
            660                 665                 670

Ser Val Asp Arg Ile Lys Ile Ala Glu Cys Asn Gly Tyr Cys Gly Gly
            675                 680                 685

Glu Gln Asn Cys Cys Thr Ala Val Lys Lys Gln Arg Lys Val Lys
            690                 695             700

Met Ile Cys Lys Asn Gly Thr Thr Lys Ile Ser Thr Val His Ile Ile
705                 710                 715                 720

Arg Gln Cys Gln Cys Glu Pro Thr Lys Ser Val Leu Ser Glu Lys
                725                 730                 735

<210> SEQ ID NO 10
<211> LENGTH: 154
<212> TYPE: PRT
<213> ORGANISM: mouse

<400> SEQUENCE: 10

Asp Pro Leu Pro Val His His Arg Cys Glu Cys Met Leu Gly Tyr Thr
 1               5                  10                  15

Gly Asp Asn Cys Ser Glu Asn Gln Asp Cys Lys Asp His Lys Cys
             20                  25                  30

Gln Asn Gly Ala Gln Cys Val Asp Glu Val Asn Ser Tyr Ala Cys Leu
             35                  40                  45

Cys Val Glu Gly Tyr Ser Gly Gln Leu Cys Glu Ile Pro Pro Ala Pro
     50                  55                  60

Arg Ser Ser Cys Glu Gly Thr Glu Cys Gln Asn Gly Ala Asn Cys Val
65                  70                  75                  80

Asp Gln Gly Ser Arg Pro Val Cys Gln Cys Leu Pro Gly Phe Gly Gly
                 85                  90                  95

Pro Glu Cys Glu Lys Leu Leu Ser Val Asn Phe Val Asp Arg Asp Thr
            100                 105                 110

Tyr Leu Gln Phe Thr Asp Leu Gln Asn Trp Pro Arg Ala Asn Ile Thr
            115                 120                 125

Leu Gln Val Ser Thr Ala Glu Asp Asn Gly Ile Leu Leu Tyr Asn Gly
        130                 135                 140

Asp Asn Asp His Ile Ala Val Glu Leu Tyr
145                 150

<210> SEQ ID NO 11
<211> LENGTH: 110
<212> TYPE: PRT
<213> ORGANISM: mouse

<400> SEQUENCE: 11

Ala Phe Lys Cys His His Gly Gln Cys His Ile Ser Asp Arg Gly Glu
 1               5                  10                  15

Pro Tyr Cys Leu Cys Gln Pro Gly Phe Ser Gly His His Cys Glu Gln
             20                  25                  30

Glu Asn Pro Cys Met Gly Glu Ile Val Arg Glu Ala Ile Arg Arg Gln
             35                  40                  45

Lys Asp Tyr Ala Ser Cys Ala Thr Ala Ser Lys Val Pro Ile Met Glu
     50                  55                  60

Cys Arg Gly Gly Cys Gly Thr Thr Cys Gln Pro Ile Arg Ser Lys
65                  70                  75                  80

Arg Arg Lys Tyr Val Phe Gln Cys Thr Asp Gly Ser Ser Phe Val Glu
                 85                  90                  95
```

```
Glu Val Glu Arg His Leu Glu Cys Gly Cys Arg Ala Cys Ser
            100                 105                 110

<210> SEQ ID NO 12
<211> LENGTH: 134
<212> TYPE: PRT
<213> ORGANISM: mouse

<400> SEQUENCE: 12

His Leu Arg Val Leu Gln Leu Met Glu Asn Arg Ile Ser Thr Ile Glu
  1               5                  10                  15

Arg Gly Ala Phe Gln Asp Leu Lys Glu Leu Glu Arg Leu Arg Leu Asn
                 20                  25                  30

Arg Asn Asn Leu Gln Leu Phe Pro Glu Leu Leu Phe Leu Gly Thr Ala
             35                  40                  45

Arg Leu Tyr Arg Leu Asp Leu Ser Glu Asn Gln Ile Gln Ala Ile Pro
         50                  55                  60

Arg Lys Ala Phe Arg Gly Ala Val Asp Ile Lys Asn Leu Gln Leu Asp
 65                  70                  75                  80

Tyr Asn Gln Ile Ser Cys Ile Glu Asp Gly Ala Phe Arg Ala Leu Arg
                 85                  90                  95

Asp Leu Glu Val Leu Thr Leu Asn Asn Asn Asn Ile Thr Arg Leu Ser
            100                 105                 110

Val Ala Ser Phe Asn His Met Pro Lys Leu Arg Thr Phe Arg Leu His
            115                 120                 125

Ser Asn Asn Leu Tyr Cys
        130

<210> SEQ ID NO 13
<211> LENGTH: 104
<212> TYPE: PRT
<213> ORGANISM: mouse

<400> SEQUENCE: 13

Asn Asn Asp Asp Cys Val Gly His Lys Cys Arg His Gly Ala Gln Cys
  1               5                  10                  15

Val Asp Glu Val Asn Gly Tyr Thr Cys Ile Cys Pro Gln Gly Phe Ser
                 20                  25                  30

Gly Leu Phe Cys Glu His Pro Pro Met Val Leu Leu Gln Thr Ser
             35                  40                  45

Pro Cys Asp Gln Tyr Glu Cys Gln Asn Gly Ala Gln Cys Ile Val Val
     50                  55                  60

Gln Gln Glu Pro Thr Cys Arg Cys Pro Pro Gly Phe Ala Gly Pro Arg
 65                  70                  75                  80

Cys Glu Lys Leu Ile Thr Val Asn Phe Val Gly Lys Asp Ser Tyr Val
                 85                  90                  95

Glu Leu Ala Ser Ala Lys Val Arg
            100

<210> SEQ ID NO 14
<211> LENGTH: 243
<212> TYPE: PRT
<213> ORGANISM: mouse

<400> SEQUENCE: 14

Ile Leu Asp Val Ala Ser Leu Arg Gln Ala Pro Gly Glu Asn Gly Thr
  1               5                  10                  15
```

-continued

```
Ser Phe His Gly Cys Ile Arg Asn Leu Tyr Ile Asn Ser Glu Leu Gln
            20                  25                  30

Asp Phe Arg Lys Met Pro Met Gln Thr Gly Ile Leu Pro Gly Cys Glu
            35                  40                  45

Pro Cys His Lys Lys Val Cys Ala His Gly Cys Cys Gln Pro Ser Ser
        50                  55                  60

Gln Ser Gly Phe Thr Cys Glu Cys Glu Glu Gly Trp Met Gly Pro Leu
 65                  70                  75                  80

Cys Asp Gln Arg Thr Asn Asp Pro Cys Leu Gly Asn Lys Cys Val His
                85                  90                  95

Gly Thr Cys Leu Pro Ile Asn Ala Phe Ser Tyr Ser Cys Lys Cys Leu
            100                 105                 110

Glu Gly His Gly Gly Val Leu Cys Asp Glu Glu Glu Asp Leu Phe Asn
            115                 120                 125

Pro Cys Gln Met Ile Lys Cys Lys His Gly Lys Cys Arg Leu Ser Gly
        130                 135                 140

Val Gly Gln Pro Tyr Cys Glu Cys Asn Ser Gly Phe Thr Gly Asp Ser
145                 150                 155                 160

Cys Asp Arg Glu Ile Ser Cys Arg Gly Glu Arg Ile Arg Asp Tyr Tyr
                165                 170                 175

Gln Lys Gln Gln Gly Tyr Ala Ala Cys Gln Thr Thr Lys Lys Val Ser
            180                 185                 190

Arg Leu Glu Cys Arg Gly Gly Cys Ala Gly Gly Gln Cys Cys Gly Pro
        195                 200                 205

Leu Arg Ser Lys Arg Arg Lys Tyr Ser Phe Glu Cys Thr Asp Gly Ser
        210                 215                 220

Ser Phe Val Asp Glu Val Glu Lys Val Val Lys Cys Gly Cys Ala Arg
225                 230                 235                 240

Cys Ala Ser
```

RECOMBINANT POLYNUCLEOTIDES ENCODING A SLIT POLYPEPTIDE

CROSS-REFERENCE TO RELATED APPLICATION

This application is a division of U.S. application Ser. No. 09/191,647, filed Nov. 13, 1998 now U.S. Pat. No. 6,046, 015, which claims the benefit of U.S. Provisional Application No. 60/081,057 filed Apr. 7, 1998 and U.S. Provisional Application No. 60/065,544, filed Nov. 14, 1997.

The research carried out in the subject application was supported in part by NIH grant NS18366. The government may have rights in any patent issuing on this application.

INTRODUCTION

1. Field of the Invention

The field of this invention is methods for modulating nerve cell function.

2. Background

In the developing CNS, most growth cones confront the midline at one or multiple times during their journey and make the decision of whether to cross or not to cross. This decision is not a static one but rather changes according to the growth cone's history. For example, in the Drosophila ventral nerve cord, about 10% of the intemneurons project their axons only on their own side, in some cases extending near the midline without crossing it The other 90% of the interneurons first project their axons across the midline and then turn to project longitudinally on the other side, often extending near the midline. These growth cones, having crossed the midline once, never cross it again, in spite of their close proximity to the midline and the many commissual axons crossing it This decision to cross or not to cross is not unique to Drosophila but is common to a variety of midline structures in all bilaterally symmetric nervous systems.

What midline signals and growth cone receptors control whether growth cones do or do not cross the midline? After crossing once, what mechanism prevents these growth cones from crossing again? A related issue concerns the nature of the midline as an intermediate target. If so many growth cones find the midline such an attractive structure, why do they cross over it rather than linger? Why do they leave the midline?

One approach to find the genes encoding the components of such a system is to screen for mutations in which either too many or too few axons cross the midline. Such a large-scale mutant screen was previously conducted in Drosophila, and led to the identification of two key genes: commissureless (comm) and roundabout (robo) (Seeger et al., 1993; reviewed by Tear et al., 1993). In comm mutant embryos, commissural growth cones initially orient toward the midline but then fail to cross it and instead recoil and extend on their own side. robo mutant embryos, on the other hand, display the opposite phenotype in that too many axons cross the midline; many growth cones that normally extend only on their own side instead now project across the midline and axons that normally cross the midline only once instead appear to cross and recross multiple times (Seeger et al, 1993; present disclosure). Double mutants of comm and robo display a robo-like phenotype.

How do comm and robo function to control midline crossing? Neither the initial paper on these genes (Seeger et al., 1993) nor the cloning of comm (Tear et al., 1996) resolved this question. comm encodes a novel surface protein expressed on midline cells. In fact, the comm paper (Tear et al., 1996) ended with the hope that future work would " . . . help shed some light on the enigmatic function of Comm."

U.S. application Ser. No. 08/971,172 (Robo, A Novel Family of Polypeptides and Nucleic Acids, by inventors: Corey S. Goodman, Thomas Kidd, Kevin J. Mitchell and Guy Tear) discloses the cloning and characterization of robo in various species including Drosophila; Robo polypeptides and polypeptide-encoding nucleic acids are also disclosed and their genbank accession numbers referenced in Kidd et al. (1998) *Cell* 92, 205–215. robo encodes a new class of guidance receptor with 5 immunoglobulin (Ig) domains, 3 fibronectin type III domains, a transmembrane domain, and a long cytoplasmic domain. Robo defines a new subfamily of Ig superfamily proteins that is highly conserved from fruit flies to mammals. The Robo ectodomains, and in particular the first two Ig domains, are highly conserved from fruit fly to human, while the cytoplasmic domains are more divergent. Nevertheless, the cytoplasmic domains contain three highly conserved short proline-rich motifs which may represent binding sites for SH3 or other binding domains in linker or signaling molecules.

For those axons that never cross the midline, Robo is expressed on their growth cones from the outset; for the majority of axons that do cross the midline, Robo is expressed at high levels on their growth cones only after they cross the midline. Transgenic rescue experiments in Drosophila reveal that Robo can function in a cell autonomous fashion, consistent with it functioning as a receptor. Thus, in Drosophila, Robo appears to function as the gatekeeper controlling midline crossing; growth cones expressing high levels of Robo are prevented from crossing the midline. Robo proteins in mammals function in a similar manner in controlling axon guidance.

U.S. application Ser. No. 60/065,54 (Methods for Modulating Nerve Cell Function, by inventors: Corey S. Goodman, Thomas Kidd, Guy Tear, Claire Russell and Kevin Mitchell now abandoned), discloses ectopic and overexpression studies revealing that Comm down-regulates Robo expression, demonstrating that Comm functions to suppress the Robo-mediated midline repulsion. These results show that the levels of Comm at the midline and Robo on growth cones are tightly intertwined and dynamically regulated to assure that only certain growth cones cross the midline, that those growth cones that cross do not linger at the midline, and that once they cross they never do so again.

Relevant Literature

Seeger, M., Tear, G., Ferres-Marco, D. and Goodman C. S. (1993) *Neuron* 10, 409–426; Tear G., et al. (1996) *Neuron* 16, 501–514; Rothberg et al. (1990) *Genes Dev* 4, 2169–2187; Kidd et al. (1998) *Cell* 92, 205–215.

SUMMARY OF THE INVENTION

The invention provides methods and compositions relating to vertebrate Slit1 and Slit2, collectively vertebrate Slit) polypeptides, related nucleic acids, polypeptide domains thereof having vertebrate Slit-specific structure and activity, and modulators of vertebrate Slit function. Vertebrate Slit polypeptides can regulate cell, especially nerve cell, function and morphology. The polypeptides may be produced recombinantly from transformed host cells from the subject vertebrate Slit polypeptide encoding nucleic acids or purified from mammalian cells. The invention provides isolated vertebrate Slit hybridization probes and primers capable of specifically hybridizing with natural vertebrate Slit genes, vertebrate Slit-specific binding agents such as specific antibodies, and methods of making and using the subject compositions in diagnosis (e.g. genetic hybridization screens for vertebrate Slit transcripts), therapy (e.g. to modulate nerve cell growth) and in the biopharmaceutical industry (e.g. as immunogens, reagents for isolating vertebrate Slit genes and polypeptides, reagents for screening chemical libraries for lead pharmacological agents, etc.).

The invention also provides methods and compositions for identifying agents which modulate the interaction of Robo and a Robo ligand and for modulating the interaction of Robo and a Robo ligand. The methods for identifying Robo:ligand modulators find particular application in commercial drug screens. These methods generally comprise (1) combining a Robo polypeptide, a Slit polypeptide and a candidate agent under conditions whereby, but for the presence of the agent, the Robo and Slit polypeptides engage in a first interaction, and (2) determining a second interaction of the Robo and Slit polypeptides in the presence of the agent, wherein a difference between the first and second interactions indicates that the aget modulates the interaction of the Robo and Slit polypeptides. The subject methods of modulating the interaction of Robo and a Robo ligand involve combining a Robo polypeptide, a Slit polypeptide and a modulator under conditions whereby, but for the presence of the modulator, the Robo and Slit polypeptides engage in a first interaction, whereby the Robo and Slit polypeptides engage in a second interaction different from the first interaction. In a particular embodiment, the modulator is dominant negative form of the Robo or Slit polypeptide.

DETAILED DESCRIPTION OF THE INVENTION

The subject methods include screens for agents which modulate Robo:ligand interactions and methods for modulating Robo:ligand interactions. Robo activation is found to regulate a wide variety of cell functions, including cell-cell interactions, cell mobility, morphology, etc. Slit polypeptides are disclosed as specific activators and inactivators of Robo polypeptides. Accordingly, the invention provides methods for modulating targeted cell function comprising the step of modulating Robo activation by contacting the cell with a modulator of a Robo:Slit interaction.

The targeted Robo polypeptide is generally naturally expressed on the targeted cells. The nucleotide sequences of exemplary natural cDNAs encoding drosophila 1, drosophila 2, C. elegans, human 1, human 2 and mouse 1 Robo polypeptides and their translates are described in Kidd et al. (1998) *Cell* 92, 205–215 and U.S. application Ser. No. 08/971,172. The targeted Robo polypeptides comprise at least a functional Robo domain, which domain has Robo-specific amino acid sequence and binding specificity or function. Preferred Robo domains comprise at least 8, preferably at least 16, more preferably at least 32, most preferably at least 64 consecutive residues of a natural fill length Robo. In a particular embodiment, the domains comprise one or more structural/functional Robo immunoglobulin, fibronectin or cytoplasmic motif domains described herein. The subject domains provide Robo-specific antigens and/or immunogens, especially when coupled to carrier proteins. For example, peptides corresponding to Robo- and human Robo-specific domains are covalently coupled to keyhole limpet antigen (KLH) and the conjugate is emulsified in Freunds complete adjuvant. Laboratory rabbits are immunized according to conventional protocol and bled. The presence of Robo-specific antibodies is assayed by solid phase immunosorbant assays using immobilized Robo polypeptides. Generic Robo-specific peptides are readily apparent as conserved regions in aligned Robo polypeptide sequences. In addition, species-specific antigenic and/or immunogenic peptides are readily apparent as diverged extracellular or cytosolic regions in alignments Human Robo-specific antibodies are characterized as uncross-reactive with non-human Robo polypeptides.

The subject domains provide Robo domain specific activity or function, such as Robo-specific cell, especially neuron modulating or modulating inhibitory activity, Robo-ligand-binding or binding inhibitory activity. Robo-specific activity or function may be determined by convenient in vitro, cell-based, or in vivo assays: e.g. in vitro binding assays, cell culture assays, in animals (e.g. gene therapy, transgenics, etc.), etc. The binding target may be a natural intracellular binding target, a Robo regulating protein or other regulator that directly modulates Robo activity or its localization; or non-natural binding target such as a specific immune protein such as an antibody, or a Robo specific agent such as those identified in screening assays such as described below. Robo-binding specificity may be assayed by binding equilibrium constants (usually at least about $10^7$ $M^{31\ 1}$, preferably at least about $10^8$ $M^{-1}$, more preferably at least about $10^9$ $M^{-1}$), by the ability of the subject polypeptide to function as negative mutants in Robo-expressing cells, to elicit Robo specific antibody in a heterologous host (e.g a rodent or rabbit), etc.

Similarly, the Slit polypeptide is conveniently selected from Slit polypeptides which specifically activate or inhibit the activation of the Robo polypeptide. Exemplary suitable Slit polypeptides (a) comprises a vertebrate Slit sequence disclosed herein, especially human Slit-1 (SEQ ID NO:02), or a deletion mutant thereof which specifically modulates Robo expression or a sequence about 60–70%, preferably about 70–80%, more preferably about 80–90%, more preferably about 90–95%, most preferably about 95–99% similar to a vertebrate Slit sequence disclosed herein as determined by Best Fit analysis using default settings and is other than a natural drosophila Slit sequence, preferably other than a natural invertebrate Slit sequence, and/or (b) is encoded by a nucleic acid comprising a natural Slit encoding sequence (such as a natural human Slit-1 encoding sequence, SEQ ID NO:01) or a fragment thereof at least 36, preferably at least 72, more preferably at least 144, most preferably at least 288 nucleotides in length which specifically hybridizes thereto. Suitable deletion mutants are readily screened in Robo binding or activation assays as described herein. Preferred Slit domains/deletion mutants/fragments comprise at least 8, preferably at least 16, more preferably at least 32, most preferably at least 64 consecutive residues of a disclosed vertebrate Slit sequences and provide a Slit specific activity, such as Slit-specific antigenicity and/or immunogenicity, especially when coupled to carrier proteins as described above for Robo above. Suitable natural Slit encoding sequence fragments are of length sufficient to encode such Slit domains. In a particular embodiment, the Slit fragments comprise species specific fragments; such fragments are readily discerned from alignments of the disclosed sequences, see, e.g. shown as unboxed sequences in Tables 1 and 2.

TABLE 1

Alignment of human Slit-1 (SEQ ID NO:02), human Slit-2 (SEQ ID NOS:03–06), Drosphila
Slit-1 (SEQ ID NO:07), C. elegans Slit-1 (SEQ ID NOS:08–09), mouse Slit-2 (SEQ ID NOS:10–11)
and mouse Slit-1 (SEQ ID NOS:12–14).

```
1    M A A P S R T T L M P P P F R L Q L R L - L I L P I L L L L R H D A V H A E    D-Slit
1    M R G V G W Q - - - - - - - M L S L S L G L V L A I L - - - - - - - - - - -    H-Slit1

40   S G G F G S S A V S S G G L G S V G I H I P G G G V G V I T E A R C P R V C S C    D-Slit
21   - - - - - - - - - - - - - - - - - - - - - - - N K V A P Q A C P A Q C S C         H-Slit1

80   T G L N V D C S H R G L T S V P R K I S A D V E R L E L Q G N N L T V I Y E T D    D-Slit
35   S G S T V D C H G L A L R S V P R N I P R N T E R L D L N G N N I T R I T K T D    H-Slit1

120  F Q R L T K L R M L Q L T D N Q I H T I E R N S F Q D L V S L E R L - - - - - -    D-Slit
74   F A G L R H L R V L Q L M E N K I S T I E R G A F Q D L K E L E R L R L N R N H    H-Slit1
1    - - - - H L R V L Q L M E N R I S T I E R G A F Q D L K E L E R L R L N R N N    M-Slit1

154  - - - - - - - - - - - - - - - - - - - D I S N N V I T T V G R R V F K G A Q S L R    D-Slit
115  L Q L F P E L L F L G T A K L Y R L D L S E N Q I Q A I P R K A F R G A V D I K    H-Slit1
36   L Q L F P E L L F L G T A R L Y R L D L S E N Q I Q A I P R K A F R G A V D I K    M-Slit1

176  S L Q L D N N Q I T C L D E H A F K G L V E L E I L T L N N N N L T S L P H N I    D-Slit
155  N L Q L D Y N Q I S C I E D G A F R A L R D L E V L T L N N N N I T R L S V A S    H-Slit1
76   N L Q L D Y N Q I S C I E D G A F R A L R D L E V L T L N N N N I T R L S V A S    M-Slit1

216  F G G L G R L R A L R L S D N P F A C D C H L S W L S R F L R S A T R L A P Y T    D-Slit
195  F N H M P K L R T F R L H S N N L Y C D C H L A W L S D W L R K R P R V G L Y T    H-Slit1
116  F N H M P K L R T F R L H S N N L Y C                                              M-Slit1

256  R C Q S P S Q L K G Q N V A D L H D Q E F K C S G L T E - H A P M - - - E C G A    D-Slit
235  Q C M G P S H L R G H N V A E V Q K R E F V C S D E E E G H Q S F M A P S C S V    H-Slit1

292  E N S C P H P C R C A D G I V D C R E K S L T S V P V T L P D D T T D V R L E Q    D-Slit
275  L H - C P A A C T C S N N I V D C R G K G L T E I P T N L P E T I T E I R L E Q    H-Slit1
1    - - - - - S P C T C S N N I V D C R G K G L M E I P A N L P E G I V E I R L E Q    H-Slit2

332  N F I T E L P P K S F S S F R R L R R I D L S N N N I S R I A H D A L S G L K Q    D-Slit
314  N T I K V I P P G A F S P Y K K L R R I D L S N N Q I S E L A P D A F Q G L R S    H-Slit1
36   N S I K A I P A G A F T Q Y K K L K R I D I S K N Q I S D I A P D A F Q G L K S    H-Slit2

372  L T T L V L Y G N K I K D L P S G V F K G L G S L R L L L N A N E I S C I R K    D-Slit
354  L N S L V L Y G N K I T E L P K S L F E G L F S L Q L L L L N A N K I N C L R V    H-Slit1
76   L T S L V L Y G N K I T E I A K G L F D G L V S L Q L L L L                        H-Slit2

1                                                                              R     CE-Slit
412  D A F R D L H S L S L L S L Y D N N I Q S L A N G T F D A M K S M K T V H L A K    D-Slit
394  D A F Q D L H N L N L L S L Y D N K L Q T I A K G T F S P L R A I Q T M H L A Q    H-Slit1

2    N P X I C D C N L Q W L A Q I N L Q K N I E T S G A R C E Q P K R L R K K K F A    CE-Slit
452  N P F I C D C N L R W L A D Y L H K N P I E T S G A R C E S P K R M H R R R I E    D-Slit
434  N P F I C D C H L K W L A D Y L H T N P I E T S G A R C T S P R R L A N K R I G    H-Slit1

42   T L P P N K F K C K G S E S F V S M Y A D S C F I D S I C P T Q C D C Y G T T V    CE-Slit
492  S L R E E K F K C S - W G E L R M K L S G E C R M D S D C P A M C H C E G T T V    D-Slit
474  Q I K S K K F R C S G T E D Y R S K L S G D C F A D L A C P E K C R C E G T T V    H-Slit1

82   D C N K R G L N T I P T S I P R F A T Q L L L S G N N I S T V D L N S N I H V L    CE-Slit
531  D C T G R R L K E I P R D I P L H T T E L L L N D N E L G R I S S D G L F G R L    D-Slit
514  D C S N Q K L N K I P E H I P Q Y T A E L R L N N N E F T V L E A T G I F K K L    H-Slit1
```

TABLE 1-continued

Alignment of human Slit-1 (SEQ ID NO:02), human Slit-2 (SEQ ID NOS:03–06), Drosphila Slit-1 (SEQ ID NO:07), *C. elegans* Slit-1 (SEQ ID NOS:08–09), mouse Slit-2 (SEQ ID NOS:10–11) and mouse Slit-1 (SEQ ID NOS:12–14).

| Pos | Sequence | Label |
|---|---|---|
| 122 | E N L E X L D L S N N H I T F I N D K S F E K L S K L R E L X L N D - - - - - - | CE-Slit |
| 571 | P H L V K L E L K R N Q L T G I E P N A F E G A S H I Q E L Q L G E N K I K E I | D-Slit |
| 554 | P Q L R K I N F S N N K I T D I E E G A F E G A S G V N E I L T S N R L E N V | H-Slit1 |
| 1 | - - - - - - - - - - - - - - - E G A F N G A A S V Q E L M L T G N Q L E T V | H-Slit2 |
| 611 | S N K M F - - - - - - - - - - - - - - - - - - - - - - L G L H Q L K T L N | D-Slit |
| 594 | Q H K M F K G - L E S L K T L M L R S N R I T C V G N D S F I G L S S V R L L S | H-Slit1 |
| 24 | H G R G F R G G L S G L K T L M L R S N L I G C V S N D T F A G L S S V R L L S | H-Slit2 |
| 626 | L Y D N Q I S C V M P G S F E H L N S L T S L N L A S N P F N C N C H L A W - F | D-Slit |
| 633 | L Y D N Q I T T V A P G A F D T L H S L S T L N L L A N P F N C N C Y L A W - L | H-Slit1 |
| 34 | L Y D N R I T T I T P G A F T T L V S L S T I N L L S N P F N C N C H L G A G L | H-Slit2 |
| 665 | A E C V R K K S L N G G A A R C G A P S K V R D V Q I K D L P H S E F K C S S E | D-Slit |
| 672 | G E W L R K K R I V T G N P R C Q K P Y F L K E I P I Q D V A I Q D F T C D D G | H-Slit1 |
| 104 | G K W L R K R R I V S G N P R C Q K P F F L K E I P I Q G V G H P G I | H-Slit2 |
| 1 | S N K N L T S F P S R I P F D | CE-Slit |
| 705 | N S E - G C L G D G Y C P P S C T C T G T V V A C S R N Q L K E I P R G I P A E | D-Slit |
| 712 | N D D N S C S P L S R C P T E C T C L D T V V R C S N K G L K V L P K G I P R D | H-Slit1 |
| 16 | T T E L Y L D A N Y I N E I P A H D L N R L Y S L T K L D L S H N R L I S L E N | CE-Slit |
| 744 | T S E L Y L E S N E I E Q I H Y E R I R H L R S L T R L D L S N N Q I T I L S N | D-Slit |
| 752 | V T E L Y L D G N Q F T L V P K E - L S N Y K H L T L I D L S N N R I S T L S N | H-Slit1 |
| 56 | N T F S N L T R L S T L I I S Y N K L R C L Q P L A F N G L N A L R I L S L H G | CE-Slit |
| 784 | Y T F A N L T K L S T L I I S Y N K L Q C L Q R H A L S G L N N L R V V S L H G | D-Slit |
| 791 | Q S F S N M T Q L L T L I L S Y N R L R C I P P R T F D G L K S L R L L S L H G | H-Slit1 |
| 96 | N D I S F L P Q S A F S N L T S I T H I A V G S N S L Y C D C N M A W F S K W I | CE-Slit |
| 824 | N R I S M L P E G S F E D L K S L T H I A L G S N P L Y C D C G L K W F S D W I | D-Slit |
| 831 | N D I S V V P E G A F N D L S A L S H L A I G A N P L Y C D C N M Q W L S D W V | H-Slit1 |
| 136 | K S K F I E A G I A R C E Y P N T V S N Q L L L T A Q P Y Q F T C D S K V P T K | CE-Slit |
| 864 | K L D Y V E P G I A R C A E P E Q M K D K L I L S T P S S S F V C R G R V R N D | D-Slit |
| 871 | K S E Y K E P G I A R C A G P G E M A D K L L L T T P S K K F T C Q G P V D V N | H-Slit1 |
| 176 | L A T K C D L C L N S P C K N N A I C E T T S S R K Y T C N C T P G F Y G V H C | CE-Slit |
| 904 | I L A K C N A C F E Q P C Q N Q A Q C V A L P Q R E Y Q C L C Q P G Y H G K H C | D-Slit |
| 911 | I L A K C N P C L S N P C K N D G T C N S D P V D F Y R C T C P Y G F K G Q D C | H-Slit1 |
| 216 | E N Q I D A C Y G S P C L N N A T C K V - - A Q A G R F N C Y C N K G F E G D Y | CE-Slit |
| 944 | E F M I D A C Y G N P C R N N A T C T V - - L E E G R F S C Q C A P G Y T G A R | D-Slit |
| 951 | D V P I H A C I S N P C K H G G T C H L K E G E E D G F W C I C A D G F E G E N | H-Slit1 |
| 254 | C E K N I D D C V N S - K C E N G G K C V D L V R F C S E E L K N F Q S F Q I N | CE-Slit |
| 982 | C E T N I D D C L G E I K C Q N N A T C I D - - - - - - - - - - - - - - - G V E | D-Slit |
| 991 | C E V N V D D C - E D N D C E N N S T C V D - - - - - - - - - - - - - - - G I N | H-Slit1 |
| 293 | S Y R C D C P M E Y E G K H C E D K L E Y C T K K L N P C E N N G K C I P I N G | CE-Slit |
| 1007 | S Y K C E C Q P G F S G E F C D T K I Q F C S P E F N P C A N G A K C M D H F T | D-Slit |
| 1015 | N Y T C L C P P E Y T G E L C E E K L D F C A Q D L N P C Q H D S K C I L T P K | H-Slit1 |
|  | D P L P V | M-Slit2 |
| 333 | S Y S C M C S P G F T G N N C E T N I D D C K N V E C Q N G G S C V D G I L S Y | CE-Slit |
| 1047 | H Y S C D C Q A G F H G T N C T D N I D D C Q N H M C Q N G G T C V D G I N D Y | D-Slit |
| 1055 | G F K C D C T P G Y V G E H C D I D F D D C Q D N K C K N G A H C T D A V N G Y | H-Slit1 |
| 1 | - - - - - - - - - - - N D D C V G H K C R H G A Q C V D E V N G Y | H-Slit2 |
| 1 | W P R C E C M P G Y A G D N C S E N Q D D C R D H K C Q N G A Q C M D E V N S Y | M-Slit2 |
| 6 | H H R C E C M L G Y T G D N C S E N Q D D C K D H K C Q N G A Q C V D E V N S Y | M-Slit2 |

TABLE 1-continued

Alignment of human Slit-1 (SEQ ID NO:02), human Slit-2 (SEQ ID NOS:03–06), Drosphila
Slit-1 (SEQ ID NO:07), *C. elegans* Slit-1 (SEQ ID NOS:08–09), mouse Slit-2 (SEQ ID NOS:10–11)
and mouse Slit-1 (SEQ ID NOS:12–14).

| Pos | Sequence | Label |
|-----|----------|-------|
| 373 | D C L C R P G Y A G Q Y C E I P P M M D M E Y Q K T D A C Q Q S A C G Q G - E C | CE-Slit |
| 1087 | Q C R C P D D Y T G K Y C E G H N M I S M M Y P Q T S P C Q N H E C K H G V - C | D-Slit |
| 1095 | T C I C P E G Y S G L F C E F S P - - P M V L P R T S P C D N F D C Q N G A Q C | H-Slit1 |
| 24 | T C I C P Q G F S G L F C E H P P - - P M V L L Q T S P C D Q Y E C Q N G A Q C | M-Slit1 |
| 41 | S C L C A E G Y S G Q L C E I P P - - H L P A P K - S P C E G T E C Q N G A N C | H-Slit2 |
| 46 | A C L C V E G Y S G Q L C E I P P - - - - - A P R - S S C E G T E C Q N G A N C | M-Slit2 |
| 412 | V A S Q N - S S D F T C K C H E G F S G P S C D R Q M S V G F K N P G A Y L A L | CE-Slit |
| 1126 | F Q P N A Q G S D Y L C R C H P G Y T G K W C E Y L T S I S F V H N N S F V E L | D-Slit |
| 1133 | I V R I N E P - - - I C Q C L P G L Y Q G E K C E K L V S V N F I N K E S Y L Q I | H-Slit1 |
| 62 | I V V Q Q E P - - - T C R C P P G F A G P R C E K L I T V N F V G K D S Y V E L | M-Slit1 |
| 78 | V D Q G N R P - - - V C Q C L P G F G G P E C E K L L S V N F V D R D T Y L Q F | H-Slit2 |
| 80 | V D Q G S R P - - - V C Q C L P G F G G P E C E K L L S V N F V D R D T Y L Q F | M-Slit2 |
| 451 | D P L A S - - D G T I T M T L R T T S K I G I L L Y Y G D D H F V S A E L Y D G | CE-Slit |
| 116 | E P L R T R P E A N V T I V F S S A E Q N G I L M Y D G Q D A H L A V E L F N G | D-Slit |
| 1170 | P S A K V R P Q T N I T L Q I A T D E D S G I L L Y K G D K D H I A V E L Y R G | H-Slit1 |
| 99 | A S A K V R | M-Slit1 |
| 115 | T D L Q N W X R X N I T L Q V F T A E D N G I L L Y N G G N D H I A V X L Y X G | H-Slit2 |
| 117 | T D L Q N W P R A N I T L Q V S T A E D N G I L L Y N G D N D H I A V E L Y | M-Slit2 |
| 489 | R V K L V Y Y I G N F P A S H M Y S S V K V N D G L P H R I S I R T S E R K C F | CE-Slit |
| 1206 | R I R V S Y D V G N H P V S T M Y S F E M V A D G K Y H A V E L L A I K K N F T | D-Slit |
| 1210 | R V R A S Y D T G S H P A S A I Y S V E T I N D G N F H I V E L L A L D Q S L S | H-Slit1 |
| 155 | H V R F S Y | M-Slit1 |
| 529 | L Q I D K N P V Q I V E N S G K S D Q L I T K G K E M L Y I G G L P I E K S Q D | CE-Slit |
| 1246 | L R V D R G L A R S I I N E G S N D Y L - - K L T T P M F L G G L P V D P A Q Q | D-Slit |
| 1250 | L S V D G G N P K I I T N L S K Q S T L - - N F D S P L Y V G G M P G K S N V A | H-Slit1 |
| 1 | I L - - - - - - - - - - - - - - - - - - - - - - - - - - - - - - - - - D V A | M-Slit1 |
| 569 | A K R F H V K N S E S L K G C I S S I T I N E V P I N L Q Q A L E N V N T E Q | CE-Slit |
| 1284 | A Y K N W Q I R N L T S F K G C M K E V W I N H K L V D F G N A Q R Q Q K I T P | D-Slit |
| 1288 | S L R Q A P G Q N G T S F H G C I R N L Y I N S E L Q D F Q K V P M Q T G I L P | H-Slit1 |
| 6 | S L R Q A P G E N G T S F H G C I R N L Y I N S E L Q D F R K M P M Q T G I L P | M-Slit1 |
| 609 | S C - - - - - - - - - - - - - - S A T V N F - - - - - - - - - - - - - - - | CE-Slit |
| 1324 | G C A L - - - - L E G E Q Q E E E D D E Q D F M D E - - - - - - T P H I K E E P | D-Slit |
| 1328 | G C E P C H K K V C A H G T C Q P S S Q A G F T C E C Q E G W M G P L C D Q R T | H-Slit1 |
| 46 | G C E P C H K K V C A H G C C Q P S S Q S G F T C E C E E G W M G P L C D Q R T | M-Slit1 |
| 617 | - - - C A G I D C G N G - K C T N N A L S P K G Y M C Q C D S H F S G E H C D E | CE-Slit |
| 1354 | V D P C L E N K C R R G S R C V P N S N A R D G Y Q C K C K H G Q R G R Y C D Q | D-Slit |
| 1368 | N D P C L G N K C V H G T - C L P I N A F - - S Y S C K C L E G H G G V L C D E | H-Slit1 |
| 86 | N D P C L G N K C V H G T - C L P I N A F - - S Y S C K C L E G H G G V L C D E | M-Slit1 |
| 653 | - - - - - - - - - - - - - - - - - - - - - - - - - - - - - - - - - - - - - | CE-Slit |
| 1394 | G E G S T E P - - - - - - - - - - - - - - - - - - - - - - - P T V T A A S - - | D-Slit |
| 1405 | E E D L F N P C Q A I K C K H G K C R L S G L G Q P Y C E C S S G Y T G D S C D | H-Slit1 |
| 123 | E E D L F N P C Q M I K C K H G K C R L S G V G Q P Y C E C N S G F T G D S C D | M-Slit1 |
| 1 | - - - - - - - - - - Q C H I S D Q G E P Y C L C Q P G F S G E H C Q | H-Slit2 |
| 1 | - - - - - - - - - - A F K C H H G Q C H I S D R G E P Y C L C Q P G F S G H H C E | M-Slit2 |
| 655 | K R I K C D K Q K F R R H H I E N E - - - - C R S V D R I K I A E C N G Y C G G | CE-Slit |
| 1405 | T - - - C R K E Q V R E Y Y T E N D - - - - C R S R Q P L K Y A K C V G G C G - | D-Slit |
| 1445 | R E I S C R G E R I R D Y Y Q K Q Q G Y A A C Q T T K V S R L E C R G G C A G | H-Slit1 |
| 163 | R E I S C R G E R I R D Y Y Q K Q Q G Y A A C Q T T K V S R L E C R G G C A G | M-Slit1 |
| 25 | Q E N P C L G Q V V R E V I R R Q K G Y A S C A T A S K V P I M E C R G G C - G | H-Slit2 |
| 32 | Q E N P C M G E I V R E A I R R Q K D Y A S C A T A S K V P I M E C R G G C - G | M-Slit2 |
| 689 | E Q N C C T A V K K Q R K V K M I C K N G T T K I S T V H I I R Q C Q C E P T | CE-Slit |
| 1440 | - N Q C C A A K I V R R R K V R M V C S N N R K Y I K N L D I V R K C G C - - T T | D-Slit |
| 1485 | G Q - C C G P L R S K R R K Y S F E C T D G S S F V D E V E K V V K C G C T R - | H-Slit1 |
| 203 | G Q - C C G P L R S K R R K Y S F E C T D G S S F V D E V E K V V K C G C A R - | M-Slit1 |
| 64 | P Q - C C Q P T R S K R R K Y V F Q C T D G S S F V E E V E R H L E C G C L A - | H-Slit2 |
| 71 | T T - C C Q P I R S K R R K Y V F Q C T D G S S F V E E V E R H L E C G C R A - | M-Slit2 |

TABLE 1-continued

Alignment of human Slit-1 (SEQ ID NO:02), human Slit-2 (SEQ ID NOS:03–06), Drosphila Slit-1 (SEQ ID NO:07), C. elegans Slit-1 (SEQ ID NOS:08–09), mouse Slit-2 (SEQ ID NOS:10–11) and mouse Slit-1 (SEQ ID NOS:12–14).

| Pos | Sequence | Label |
|---|---|---|
| 729 | K S V L - - S E K | CE-Slit |
| 1477 | K K C Y | D-Slit |
| 1523 | - - - - C V S | H-Slit1 |
| 241 | - - - - C A S | M-Slit1 |
| 102 | - - - - C - S | H-Slit2 |
| 109 | - - - - C - S | M-Slit2 |

TABLE 2

Alignment of human Slit-1 (SEQ ID NO:02) and Drosphila Slit-1 (SEQ ID NO:07)

| Pos | Sequence | Label |
|---|---|---|
| 1 | M A A P S R T T L M P P P F R L Q L R L - L I L P I L L L R H D A V H A E | D-Slit |
| 1 | M R G V G W Q - - - - - - - M L S L S L G L V L A I L - - - - - - - - - - | H-Slit1 |
| 40 | S G G F G S S A V S S G G L G S V G I H I P G G G V G V I T E A R C P R V C S C | D-Slit |
| 21 | - - - - - - - - - - - - - - - - - - - - - - - - - - N K V A P Q A C P A Q C S C | H-Slit1 |
| 80 | T G L N V D C S H R G L T S V P R K I S A D V E R L E L Q G N N L T V I Y E T D | D-Slit |
| 35 | S G S T V D C H G L A L R S V P R N I P R N T E R L D L N G N N I T R I T K T D | H-Slit1 |
| 120 | F Q R L T K L R M L Q L T D N Q I H T I E R N S F Q D L V S L E R L - - - - - - | D-Slit |
| 75 | F A G L R H L R V L Q L M E N K I S T I E R G A F Q D L K E L E R L R L N R N H | H-Slit1 |
| 154 | - - - - - - - - - - - - - - - - - - - D I S N N V I T T V G R V F K G A Q S L R | D-Slit |
| 115 | L Q L F P E L L F L G T A K L Y R L D L S E N Q I Q A I P R K A F R G A V D I K | H-Slit1 |
| 176 | S L Q L D N N Q I T C L D E H A F K G L V E L E I L T L N N N L T S L P H N I | D-Slit |
| 155 | N L Q L D Y N Q I S C I E D G A F R A L R D L E V L T L N N N I T R L S V A S | H-Slit1 |
| 216 | F G G L G R L R A L R L S D N P F A C D C H L S W L S R F L R S A T R L A P Y T | D-Slit |
| 195 | F N H M P K L R T F R L H S N N L Y C D C H L A W L S D W L R K R P R V G L Y T | H-Slit1 |
| 256 | R C Q S P S Q L K G Q N V A D L H D Q E F K C S G L T E - H A P M - - - E C G A | D-Slit |
| 235 | Q C M G P S H L R G H N V A E V Q K R E F V C S D E E E G H Q S F M A P S C S V | H-Slit1 |
| 292 | E N S C P H P C R C A D G I V D C R E K S L T S V P V T L P D D T T D V R L E Q | D-Slit |
| 275 | L H - C P A A C T C S N N I V D C R G K G L T E I P T N L P E T I T E I R L E Q | H-Slit1 |
| 332 | N F I T E L P P K S F S S F R R L R R I D L S N N N I S R I A H D A L S G L K Q | D-Slit |
| 314 | N T I K V I P P G A F S P Y K K L R R I D L S N N Q I S E L A P D A F Q G L R S | H-Slit1 |
| 372 | L T T L V L Y G N K I K D L P S G V F K G L G S L R L L L L N A N E I S C I R K | D-Slit |
| 354 | L N S L V L Y G N K I T E L P K S L F E G L F S L Q L L L L N A N K I N C L R V | H-Slit1 |
| 412 | D A F R D L H S L S L L L S L Y D N N I Q S L A N G T F D A M K S M K T V H L A K | D-Slit |
| 394 | D A F Q D L H N L N L L L S L Y D N K L Q T I A K G T F S P L R A I Q T M H L A Q | H-Slit1 |
| 452 | N P F I C D C N L R W L A D Y L H K N P I E T S G A R C E S P K R M H R R R I E | D-Slit |
| 434 | N P F I C D C H L K W L A D Y L H T N P I E T S G A R C T S P R R L A N K R I G | H-Slit1 |
| 492 | S L R E E K F K C S - W G E L R M K L S G E C R M D S D C P A M C H C E G T T V | D-Slit |
| 474 | Q I K S K K F R C S G T E D Y R S K L S G D C F A D L A C P E K C R C E G T T V | H-Slit1 |
| 531 | D C T G R R L K E I P R D I P L H T T E L L L N D N E L G R I S S D G L F G R L | D-Slit |
| 514 | D C S N Q K L N K I P E H I P Q Y T A E L R L N N N E F T V L E A T G I F K K L | H-Slit1 |

TABLE 2-continued

Alignment of human Slit-1 (SEQ ID NO:02) and Drosphila Slit-1 (SEQ ID NO:07)

```
571   P H L V K L E L K R N Q L T G I E P N A F E G A S H I Q E L Q L G E N K I K E I        D-Slit
554   P Q L R K I N F S N N K I T D I E E G A F E G A S G V N E I L L T S N R L E N V        H-Slit1

511   S N K M F L G L H Q L K T L - - - - - - - - - - - - - - - - - - - - - - N L            D-Slit
594   Q H K M F K G L E S L K T L M L R S N R I T C V G N D S F I G L S S V R L L S L        H-Slit1

627   Y D N Q I S C V M P G S F E H L N S L T S L N L A S N P F N C N C H L A W F A E        D-Slit
634   Y D N Q I T T V A P G A F D T L H S L S T L N L L A N P F N C N C Y L A W L G E        H-Slit1

667   C V R K K S L N G G A A R C G A P S K V R D V Q I K D L P H S E F K C S S E N S        D-Slit
674   W L R K K R I V T G N P R C Q K P Y F L K E I P I Q D V A I Q D F T C D D G N D        H-Slit1

707   E - G C L G D G Y C P P S C T C T G T V V A C S R N Q L K E I P R G I P A E T S        D-Slit
714   D N S C S P L S R C P T E C T C L D T V V R C S N K G L K V L P K G I P R D V T        H-Slit1

746   E L Y L E S N E I E Q I H Y E R I R H L R S L T R L D L S N N Q I T I L S N Y T        D-Slit
754   E L Y L D G N Q F T L V P K E - L S N Y K H L T L I D L S N N R I S T L S N Q S        H-Slit1

786   F A N L T K L S T L I I S Y N K L Q C L Q R H A L S G L N N L R V V S L H G N R        D-Slit
793   F S N M T Q L L T L I L S Y N R L R C I P P R T F D G L K S L R L L S L H G N D        H-Slit1

826   I S M L P E G S F E D L K S L T H I A L G S N P L Y C D C G L K W F S D W I K L        D-Slit
833   I S V V P E G A F N D L S A L S H L A I G A N P L Y C D C N M Q W L S D W V K S        H-Slit1

866   D Y V E P G I A R C A E P E Q M K D K L I L S T P S S S F V C R G R V R N D I L        D-Slit
873   E Y K E P G I A R C A G P G E M A D K L L L T T P S K K F T C Q G P V D V N I L        H-Slit1

906   A K C N A C F E Q P C Q N Q A Q C V A L P Q R E Y Q C L C P G Y H G K H C E F          D-Slit
913   A K C N P C L S N P C K N D G T C N S D P V D F Y R C T C P Y G F K G Q D C D V        H-Slit1

946   M I D A C Y G N P C R N N A T C T V L E - - E G R F S C Q C A P G Y T G A R C E        D-Slit
953   P I H A C I S N P C K H G G T C H L K E G E E D G F W C I C A D G F E G E N C E        H-Slit1

984   T N I D D C L G E I K C Q N N A T C I D G V E S Y K C E C Q P G F S G E F C D T        D-Slit
993   V N V D D C - E D N D C E N N S T C V D G I N N Y T C L C P P E Y T G E L C E E        H-Slit1

1024  K I Q F C S P E F N P C A N G A K C M D H F T H Y S C D C Q A G F H G T N C T D        D-Slit
1032  K L D F C A Q D L N P C Q H D S K C I L T P K G F K C D C T P G Y V G E H C D I        H-Slit1

1064  N I D D C Q N H M C Q N G G T C V D G I N D Y Q C R C P D D Y T G K Y C E G H N        D-Slit
1072  D F D D C Q D N K C K N G A H C T D A V N G Y T C I C P E G Y S G L F C E F S P        H-Slit1

1104  M I S M M Y P Q T S P C Q N H E C K H G V - C F Q P N A Q G S D Y L C R C H P G        D-Slit
1112  - - P M V L P R T S P C D N F D C Q N G A Q C I - - - V R I N E P I C Q C L P G        H-Slit1

1143  Y T G K W C E Y L T S I S F V H N N S F V E L E P L R T R P E A N V T I V F S S        D-Slit
1147  Y Q G E K C E K L V S V N F I N K E S Y L Q I P S A K V R P Q T N I T L Q I A T        H-Slit1

1183  A E Q N G I L M Y D G Q D A H L A V E L F N G R I R V S Y D V G N H P V S T M Y        D-Slit
1187  D E D S G I L L Y K G D K D H I A V E L Y R G R V R A S Y D T G S H P A S A I Y        H-Slit1

1223  S F E M V A D G K Y H A V E L L A I K K N F T L R V D R G L A R S I I N E G S N        D-Slit
1227  S V E T I N D G N F H I V E L L A L D Q S L S L S V D G G N P K I I T N L S K Q        H-Slit1

1263  D Y L K L T T P M F L G G L P V D P A Q Q A Y K N W Q I R N L T S F K G C M K E        D-Slit
1267  S T L N F D S P L Y V G G M P G K S N V A S L R Q A P G Q N G T S F H G C I R N        H-Slit1
```

TABLE 2-continued

Alignment of human Slit-1 (SEQ ID NO:02) and Drosphila Slit-1 (SEQ ID NO:07)

```
1303  V W I N H K L V D F G N A Q R Q Q K I T P G C A L - - - - L E G E Q Q E E E D D    D-Slit
1307  L Y I N S E L Q D F Q K V P M Q T G I L P G C E P C H K K V C A H G T C Q P S S    H-Slit1

1339  E Q D F M D E - - - - - - T P H I K E E P V D P C L E N K C R R G S R C V P N S    D-Slit
1347  Q A G F T C E C Q E G W M G P L C D Q R T N D P C L G N K C V H G T - C L P I N    H-Slit1

1376  N A R D G Y Q C K C K H G Q R G R Y C D Q G E G S T E P - - - - - - - - - - - -    D-Slit
1386  A F - - S Y S C K C L E G H G G V L C D E E E D L F N P C Q A I K C K H G K C R    H-Slit1

1401  - - - - - - - - - - - - - P T V T A A S - - - - - T C R K E Q V R E Y Y T E N D -  D-Slit
1424  L S G L G Q P Y C E C S S G Y T G D S C D R E I S C R G E R I R D Y Y Q K Q Q G    H-Slit1

1423  - - - C R S R Q P L K Y A K C V G G C - G N Q C C A A K I V R R R K V R M V C S    D-Slit
1464  Y A A C Q T T K K V S R L E C R G G C A G G Q C C G P L R S K R R K Y S F E C T    H-Slit1

1459  N N R K Y I K N L D I V R K C G C T K K C Y                                        D-Slit
1504  D G S S F V D E V E K V V K C G C T R - C V S                                      H-Slit1
```

Exemplary such human Slit-1 immunogenic and/or antigenic peptides are shown in Table 3.

TABLE 3

Immunogenic human Slit-1 polypeptides eliciting Slit-1 specific rabbit polyclonal antibody: Slit polypeptide-KLH conjugates immunized per-protocol described above.

| Slit Polypeptide | Immunogenicity | Slit Polypeptide | Immunogenicity |
|---|---|---|---|
| SEQ ID NO:02, res. 1–10 | +++ | SEQ ID NO:02, res. 561–576 | +++ |
| SEQ ID NO:02, res. 29–41 | +++ | SEQ ID NO:02, res. 683–697 | +++ |
| SEQ ID NO:02, res. 75–87 | +++ | SEQ ID NO:02, res. 768–777 | +++ |
| SEQ ID NO:02, res. 92–109 | +++ | SEQ ID NO:02, res. 798–813 | +++ |
| SEQ ID NO:02, res. 132–141 | +++ | SEQ ID NO:02, res. 882–894 | +++ |
| SEQ ID NO:02, res. 192–205 | +++ | SEQ ID NO:02, res. 934–946 | +++ |
| SEQ ID NO:02, res. 258–269 | +++ | SEQ ID NO:02, res. 1054–1067 | +++ |
| SEQ ID NO:02, res. 295–311 | +++ | SEQ ID NO:02, res. 1181–1192 | +++ |
| SEQ ID NO:02, res. 316–330 | +++ | SEQ ID NO:02, res. 1273–1299 | +++ |
| SEQ ID NO:02, res. 373–382 | +++ | SEQ ID NO:02, res. 1383–1397 | +++ |
| SEQ ID NO:02, res. 403–422 | +++ | SEQ ID NO:02, res. 1468–1477 | +++ |
| SEQ ID NO:02, res. 474–485 | +++ | SEQ ID NO:02, res. 1508–1517 | +++ |

The subject domains provide Slit domain specific activity or function, such as Slit-specific cell, especially neuron modulating or modulating inhibitory activity, Slit-ligand-binding or binding inhibitory activity. Slit-specific activity or function may be determined by convenient in vitro, cell-based, or in vivo assays: e.g. in vitro binding assays, cell culture assays, in animals (e.g. gene therapy, transgenics, etc.), etc. The binding target may be a natural intracellular binding target, a Slit regulating protein or other regulator that directly modulates Slit activity or its localization; or non-natural binding target such as a specific immune protein such as an antibody, or a Slit specific agent such as those identified in screening assays such as described below. Slit-binding specificity may be assayed by binding equilibrium constants (usually at least about $10^7$ $M^{-1}$, preferably at least about $10^8$ $M^{-1}$, more preferably at least about $10^9$ $M^{-1}$), by the ability of the subject polypeptide to function as negative mutants in Slit-expressing cells, to elicit Slit specific antibody in a heterologous host (e.g a rodent or rabbit), etc.

In one embodiment, the Slit polypeptides are encoded by a nucleic acid comprising SEQ ID NO:01 or a fragment thereof which hybridizes with a full-length strand thereof, preferably under stringent conditions. Such nucleic acids comprise at least 36, preferably at least 72, more preferably at least 144 and most preferably at least 288 nucleotides of SEQ ID NO:01. Demonstrating specific hybridization generally requires stringent conditions, for example, hybridizing in a buffer comprising 30% formamide in 5× SSPE (0.18M NaCl, 0.01M NaPO$_4$, pH7.7, 0.001M EDTA) buffer at a temperature of 42° C. and remaining bound when subject to washing at 42° C. with 0.2× SSPE (Conditions I); preferably hybridizing in a buffer comprising 50% formamide in 5× SSPE buffer at a temperature of 42° C. and remaining bound when subject to washing at 42° C. with 0.2× SSPE buffer at 42° C. (Conditions II). Exemplary nucleic acids which hybridize with a strand of SEQ ID NO:01 are shown in Table 4.

TABLE 4

Exemplary nucleic acids which hybridize with a strand of SEQ ID NO:01 under Conditions I and/or II.

| Slit Nucleic Acid | Hybridization | Slit Nucleic Acid | Hybridization |
| --- | --- | --- | --- |
| SEQ ID NO:01, nucl. 1–47 | + | SEQ ID NO:01, nucl. 1258–1279 | + |
| SEQ ID NO:01, nucl. 58–99 | + | SEQ ID NO:01, nucl. 1375–1389 | + |
| SEQ ID NO:01, nucl. 95–138 | + | SEQ ID NO:01, nucl. 1581–1595 | + |
| SEQ ID NO:01, nucl. 181–220 | + | SEQ ID NO:01, nucl. 1621–1639 | + |
| SEQ ID NO:01, nucl. 261–299 | + | SEQ ID NO:01, nucl. 1744–1755 | + |
| SEQ ID NO:01, nucl. 274–315 | + | SEQ ID NO:01, nucl. 1951–1969 | + |
| SEQ ID NO:01, nucl. 351–389 | + | SEQ ID NO:01, nucl. 2150–2163 | + |
| SEQ ID NO:01, nucl. 450–593 | + | SEQ ID NO:01, nucl. 2524–2546 | + |
| SEQ ID NO:01, nucl. 524–546 | + | SEQ ID NO:01, nucl. 2761–2780 | + |
| SEQ ID NO:01, nucl. 561–608 | + | SEQ ID NO:01, nucl. 2989–2999 | + |
| SEQ ID NO:01, nucl. 689–727 | + | SEQ ID NO:01, nucl. 3108–3117 | + |
| SEQ ID NO:01, nucl. 708–737 | + | SEQ ID NO:01, nucl. 3338–3351 | + |
| SEQ ID NO:01, nucl. 738–801 | + | SEQ ID NO:01, nucl. 3505–3514 | + |
| SEQ ID NO:01, nucl. 805–854 | + | SEQ ID NO:01, nucl. 3855–3867 | + |
| SEQ ID NO:01, nucl. 855–907 | + | SEQ ID NO:01, nucl. 4010–4025 | + |
| SEQ ID NO:01, nucl. 910–953 | + | SEQ ID NO:01, nucl. 4207–4219 | + |
| SEQ ID NO:01, nucl. 1007–1059 | + | SEQ ID NO:01, nucl. 4333–4345 | + |
| SEQ ID NO:01, nucl. 1147–1163 | + | SEQ ID NO:01, nucl. 4521–4529 | + |

A wide variety of cell types express Robo polypeptides subject to regulation by the disclosed methods, including many neuronal cells, transformed cells, infected (e.g. virus) cells, etc. Ascertaining Robo binding or activation is readily effected by binding assays or cells function assays as disclosed herein or in the cited copending applications. Accordingly, indications for the subject methods encompass a wide variety of cell types and function, including axon outgrowth, tumor cell invasion or migration, etc. The target cell may reside in culture or in situ, i.e. within the natural host. For in situ applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Slit polypeptides may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, embedding or derivatizing fibers, such as collagen fibers, protein polymers, etc. with therapeutic polypeptides. Other useful approaches are described in Otto et al. (1989) *J Neuroscience Research* 22, 83–91 and Otto and Unsicker (1990) *J Neuroscience* 10, 1912–1921. Generally, the amount administered will be empirically determined, typically in the range of about 10 to 1000 µg/kg of the recipient and the concentration will generally be in the range of about 50 to 500 µg/ml in the dose administered. Other additives may be included, such as stabilizers, bactericides, etc. will be present in conventional amounts.

In one embodiment, the invention provides administering the subject Slit polypeptides in combination with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. In another embodiment, the invention provides the subject compounds in the form of a prodrag, which can be metabolically converted to the subject compound by the recipient host. A wide variety of pro-drug formulations for polypeptide-based therapeutics are known in the art. The compositions may be provided in any convenient form including tablets, capsules, troches, powders, sprays, creams, etc. As such the compositions, in pharmaceutically acceptable dosage units or in bulk, may be incorporated into a wide variety of containers. For example, dosage units may be included in a variety of containers including capsules, pills, etc. The compositions may be advantageously combined and/or used in combination with other therapeutic or prophylactic agents, different from the subject compounds. In many instances, administration in conjunction with the subject compositions enhances the efficacy of such agents, see e.g. Goodman & Gilman's The Pharmacological Basis of Therapeutics, $9^{th}$ Ed., 1996, McGraw-Hill.

In another aspect, the invention provides methods of screening for agents which modulate Robo-Slit interactions. These methods generally involve forming a mixture of a Robo-expressing cell, a Slit polypeptide and a candidate agent, and determining the effect of the agent on the amount of Robo expressed by the cell. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Cell and animal based neural guidance/repulsion assays are described in detail in the experimental section below.

The amino acid sequences of the disclosed vertebrate Slit polypeptides are used to back-translate Slit polypeptide-encoding nucleic acids optimized for selected expression systems (Holler et al. (1993) *Gene* 136, 323–328; Martin et al. (1995) *Gene* 154, 150–166) or used to generate degenerate oligonucleotide primers and probes for use in the isolation of natural Slit-encoding nucleic acid sequences ("GCG" software, Genetics Computer Group, Inc, Madison Wis.). Slit-encoding nucleic acids used in Slit-expression vectors and incorporated into recombinant host cells, e.g. for expression and screening, transgenic animals, e.g. for functional studies such as the efficacy of candidate drugs for disease associated with Slit-modulated cell function, etc.

The invention also provides nucleic acid hybridization probes and replication/amplification primers having a vertebrate Slit cDNA specific sequence comprising a fragment of a disclosed vertebrate cDNA sequence, and sufficient to effect specific hybridization thereto. Such primers or probes are at least 12, preferably at least 24, more preferably at least 36 and most preferably at least 96 nucleotides in length. Demonstrating specific hybridization generally requires stringent conditions, for example, hybridizing in a buffer comprising 30% formamide in 5× SSPE (0.18M NaCl, 0.01M NaPO$_4$, pH7.7, 0.001M EDTA) buffer at a temperature of 42° C. and remaining bound when subject to washing at 42° C. with 0.2× SSPE; preferably hybridizing in a buffer comprising 50% formamide in 5× SSPE buffer at a temperature of 42° C. and remaining bound when subject to washing at 42° C. with 0.2× SSPE buffer at 42° C. Slit nucleic acids can also be distinguished using alignment algorithms, such as BLASTX (Altschul et al. (1990) Basic Local Alignment Search Tool, *J Mol Biol* 215, 403–410). In addition, the invention provides nucleic acids having a sequence about 60–70%, preferably about 70–80%, more preferably about 80–90%, more preferably about 90–95%, most preferably about 95–99% similar to a vertebrate Slit sequence disclosed herein as determined by Best Fit analysis using default settings and is other than a natural drosophila Slit sequence, preferably other than a natural invertebrate Slit sequence. In a particular embodiment, the Slit polynucleotide fragments comprise species specific fragments; such fragments are readily discerned from alignments of the disclosed sequences.

The subject nucleic acids are of synthetic/non-natural sequences and/or are recombinant, meaning they comprise a non-natural sequence or a natural sequence joined to nucleotide(s) other than that which it is joined to on a natural chromosome. The subject recombinant nucleic acids comprising the nucleotide sequence of disclosed vertebrate Slit nucleic acids, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, more preferably fewer than 500 bp, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of Slit genes and gene transcripts and in detecting or amplifying nucleic acids encoding additional Slit homologs and structural analogs. In diagnosis, Slit hybrdization probes find use in identifying wild-type and mutant Slit alleles in clinical and laboratory samples. Mutant alleles are used to generate allele-specific oligonucleotide (ASO) probes for high-throughput clinical diagnoses. In therapy, therapeutic Slit nucleic acids are used to modulate cellular expression or intracellular concentration or availability of active Slit. Exemplary human Slit-1 probes and primers are shown in Table 5 and Table 6.

TABLE 5

Hybridization Probes for Regions of Human Slit-1.

| | |
|---|---|
| Hybridization probe for first leucine rich repeat region | SEQ ID NO:01, nucleotides 82–828 |
| Hybridization probe for second leucine rich repeat region | SEQ ID NO:01, nucleotides 829–1503 |
| Hybridization probe for third leucine rich repeat region | SEQ ID NO:01, nucleotides 1504–2166 |
| Hybridization probe for fourth leucine rich repeat region | SEQ ID NO:01, nucleotides 2167–2751 |
| Hybridization probe for EGF repeats one to five | SEQ ID NO:01, nucleotides 2752–3327 |
| Hybridization probe for the sixth EGF repeat and preceding spacer region | SEQ ID NO:01, nucleotides 3328–3461 |
| Hybridization probe for the 99aa spacer/G-loop region | SEQ ID NO:01, nucleotides 3462–3987 |
| Hybridization probe for EGF repeats seven to nine | SEQ ID NO:01, nucleotides 3988–4341 |
| Hybridization probe for the cysteine knot region | SEQ ID NO:01, nucleotides 4342–4575 |

TABLE 6

PCR Primers for regions of Human Slit.

| | |
|---|---|
| PCR Primers for first leucine rich repeat region | Forward: SEQ ID NO:01, nucleotides 82–111<br>Reverse: reverse complement of SEQ ID NO:01, nucleotides 799–828 |
| PCR Primers for second leucine rich repeat region | Forward: SEQ ID NO:01, nucleotides 829–858<br>Reverse: reverse complement of SEQ ID NO:01, nucleotides 1474–1503 |
| PCR Primers for third leucine rich repeat region | Forward: SEQ ID NO:01, nucleotides 1504–1533<br>Reverse: reverse complement of SEQ ID NO:01, nucleotides 2137–2166 |
| PCR Primers for fourth leucine rich repeat region | Forward: SEQ ID NO:01, nucleotides 2167–2196<br>Reverse: reverse complement of SEQ ID NO:01, nucleotides 2722–2751 |
| PCR Primers for EGF repeats one to five | Forward: SEQ ID NO:01, nucleotides 2752–2781<br>Reverse: reverse complement of SEQ ID NO :01, nucleotides 3298–3327 |
| PCR Primers for the sixth EGF repeat and preceding spacer region | Forward: SEQ ID NO:01, nucleotides 3328–3357<br>Reverse: reverse complement of SEQ ID NO:01, nucleotides 3432–3461 |
| PCR Primers for the 99aa spacer/G-loop region | Forward: SEQ I:01, nucleotides 3462–3491<br>Reverse: reverse complement of SEQ ID NO:01, nucleotides 3958–3987 |
| PCR Primers for EGF repeats seven to nine | Forward: SEQ ID NO:01, nucleotides 3988–4017<br>Reverse: reverse complement of SEQ ID NO:01, nucleotides 4312–4341 |
| PCR Primers for the cysteine knot region | Forward: SEQ ID NO:01, nucleotides 4342–4371<br>Reverse: reverse complement of SEQ ID NO:01, nucleotides 4546–4575 |

Leucine rich repeats (LRRs) are predicted by comparison with known proteins and by the presence of a leucine rich core sequence. In slit proteins, the LRRs are flanked by conserved sequences referred to as the amino- and carboxy-flanking regions. These flanking regions are found in other known proteins, but only in a few instances are both the amino- and carboxy-flank regions present in a single protein. The so called "99aa spacer" is actually ~200 amino acids in the Drosophila protein and 174 amino acids in Human Slit-1. This region shows homology to the G-loops of laminin A chains.

Cysteine knots are dimerisation domains defined by the presence of six cysteine residues between which disulphide bridges form. The only absolutely conserved residues are the six cysteines, and spacing between them is highly variable, apart from between cysteines 2 and 3, and 5 and 6. The glycine between cysteines 2 and 3 is only present in a subset of cysteine knots. Drosophila slit and Human slit-1 both have an extra cysteine after cysteines 5 and 6: this may serve as an intermolecular bond. Human Slit-1 gene displays the overall structure of the Drosophila gene, and amino acid conservation is found along the entire length of the protein (48% homology at the amino acid sequence excluding the signal sequence; see below). The Human gene has an extra LRR between LRR2 and LRR3 of the first set of LRRs; in the third set, the Human gene has an extra LRR between LRR3 and LRR4. The Human gene has two extra EGF repeats, on either side of the seventh EGF repeat in Drosophila slit.

Isolation of Human slit-1

Searching of the EST database revealed an EST, ab16g10.r1, with homology to the 99aa spacer region of Drosophila slit. This EST was used to probe a Human fetal brain library (Stratagene), and clones for Human slit-1 were isolated.

Features of Human Slit Predicted Protein

| | |
|---|---|
| Signal sequence | SEQ ID NO:02, residues 7–24 |
| First amino-flanking sequence | SEQ ID NO:02, residues 28–59 |
| First set of Leucine Rich Repeats | SEQ ID NO:02, residues 60–179 (6 repeats) |
| First carboxy-flanking sequence | SEQ ID NO:02, residues 180–276 |
| Second amino-flanking sequence | SEQ ID NO:02, residues 277–308 |
| Second set of Leucine Rich Repeats | SEQ ID NO:02, residues 309–434 (5 repeats) |
| Second carboxy-flanking sequence | SEQ ID NO:02, residues 435–501 |
| Third amino-flanking sequence | SEQ ID NO:02, residues 502–533 |
| Third set of Leucine Rich Repeats | SEQ ID NO:02, residues 534–560 (5 repeats) |
| Third carboxy-flanking sequence | SEQ ID NO:02, residues 661–722 |
| Fourth amino-flanking sequence | SEQ ID NO:02, residues 723–754 |
| Fourth set of Leucine Rich Repeats | SEQ ID NO:02, residues 755–855 (4 repeats) |
| Fourth carboxy-flanking sequence | SEQ ID NO:02, residues 856–917 |
| First EGF repeat | SEQ ID NO:02, residues 918–952 |
| Second EGF repeat | SEQ ID NO:02, residues 953–993 |
| Third EGF repeat | SEQ ID NO:02, residues 994–1031 |
| Fourth EGF repeat | SEQ ID NO:02, residues 1032–1071 |
| Fifth EGF repeat | SEQ ID NO:02, residues 1072–1109 |
| Spacer | SEQ ID NO:02, residues 1110–1116 |
| Sixth EGF repeat | SEQ ID NO:02, residues 1117–1153 |
| "99aa spacer" | SEQ ID NO:02, residues 1155–1329 |
| Seventh EGF repeat | SEQ ID NO:02, residues 1330–1366 |
| Eighth EGF repeat | SEQ ID NO:02, residues 1367–1404 |
| Nineth EGF repeat | SEQ ID NO:02, residues 1405–1447 |
| Cysteine knot motif | SEQ ID NO:02, residues 1448–1525 |
| Amino acid identity between Drosophila and Human Slit-1 | |
| First amino-flanking sequence | 53% |
| First set of Leucine Rich Repeats | 52% (54%, 67%, NA, 38%, 54%, 50%) |
| First carboxy-flanking sequence | 42% |
| Second amino-flanking sequence | 50% |
| Second set of Leucine Rich Repeats | 60% (54%, 58%, 67%, 71%, 50%) |
| Second carboxy-flanking sequence | 62% |
| Third amino-flanking sequence | 56% |
| Third set of Leucine Rich Repeats | 49% (46%, 46%, 42%, NA, 58%) |
| Third carboxy-flanking sequence | 36% |
| Fourth amino-flanking sequence | 53% |
| Fourth set of Leucine Rich Repeats | 48% (25%, 58%, 46%, 63%) |
| Fourth carboxy-flanking sequence | 63% |
| First EGF repeat | 34% |
| Second EGF repeat | 46% |
| Third EGF repeat | 46% |
| Fourth EGF repeat | 35% |
| Fifth EGF repeat | 47% |
| Spacer | 22% |
| Sixth EGF repeat | 40% |
| "99aa spacer" | 38% |
| Seventh EGF repeat | 11%/NA |
| Eighth EGF repeat | 44% |
| Nineth EGF repeat | 29%/NA |
| Cysteine knot motif | 34% |

NA: not applicable due to absence of homologous repeat. Figures for individual LLRs are shown in brackets.

The following examplary assay is offered by way of illustration and not by way of limitation:

EXAMPLES

Protocol for Ligand Screening of Transfected COS cells.

I. Prepare the Ligand

Expression Construct: cDNAs encoding targeted Slit polypeptides are tagged with the Fc portion of human IgG and subcloned into a 293 expression vector (pCEP4: In Vitrogen).

Transfection: 293 EBNA cells are transfected (CaPO$_4$ method) with the Slit expression constructs. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Prepare Truncated Receptor (Positive Control)

Expression Construct: cDNA encoding a corresponding Robo C-terminal deletion mutant comprising the extracellular domain (truncated immediately N-terminal to the transmembrane region) is subcloned into a 293 expression vector (pCEP4: In Vitrogen).

Transfection: 293 EBNA cells are transfected (CaPO$_4$ method) with the receptor mutant expression construct. After 24 h recovery, transfected cells are selected with G418 geneticin, 250 ug/ml, Gibco) and hygromycin (200 ug/ml). Once the selection process is complete, cells are maintained in Dulbecco's Modified Eagles medium (D)ME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Transfect COS Cells

Seed COS cells (250,000) on 35 mm dishes in 2 ml DME/10% FCS.

18–24 h later, dilute 1 ug of Robo-encoding DNA (cDNA cloned into pMT21 expression vector) into 200 ul serum-free media and add 6 ul of Lipofectanune (Gibco). Incubate this solution at room temperature for 15–45 min.

Wash the cells 2× with PBS. Add 800 ul serum-free media to the tube containing the lipid-DNA complexes. Overlay this solution onto the washed cells.

Incubate for 6 h. Stop the reaction by adding 1 ml DMA/20% FCS. Refeed cells. Assay cells 12 hr later.

III. Ligand Binding Assay

Wash plates of transfected COS cells 1× with cold PBS (plus Ca/Mg)/1% goat serum. Add 1 ml conditioned media neat and incubate 90 min at room temp.

Wash plates 3× with PBS (plus Ca/Mg). On the 4th wash, add 1 ml 50% methanol to 1 ml PBS. Then add 1 ml methanol. Evacuate and add 1 ml methanol.

Wash 1× with PBS. Wash 1× PBS/1% goat serum

Add secondary antibody (1-to-2,000 anti-human Fc conjugated to alkaline phosphatase (Jackson Lab)) in PBS/1% goat serum. Incubate 30–40 min room temp.

Wash 3× with PBS. Wash 1× alkaline phosphatase buffer (100 mM Tris-Cl, pH 9.5, 100 mM NaCl, 5 mM MgCl). Prepare alkaline phosphatase reagents: 4.5 ul/ml NBT and 3.5 ul/ml BCIP (Gibco) in alkaline phosphatase buffer.

Incubate 10–30 min, quench with 20 mM EDTA in PBS. Cells that have bound Slit polypeptides are visible by the presence of a dark purple reaction product.

In parallel incubations, positive controls are provided by titrating Slit binding with serial dilutions of the mutant receptor conditioned medium.

IV. Results: Binding of Slit to Robo

Cell expressing mammalian Slit polypeptides were shown to bind Robo. No reactivity was observed with control COS cells or with receptor-expressing COS cells in the presence of the secondary antibody but in the absence of the Slit-Fc fusion. Binding was observed to receptor-expression cells using a construct in which a Slit polypeptide is fused directly to alkaline phosphatase, for which a secondary antibody is not required. Receptor deletion mutants titrate the Slit-Robo binding, serving as a positive control for inhibition assays.

Protocol for high throughput Robo-Slit binding assay

A. Reagents

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.

$^{33}$P Robo polypeptide 10× stock: $10^{-8}$–$10^{-6}$M "cold" Robo polypeptide specific Robo domain supplemented with 200,000–250,000 cpm of labeled Robo (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB #917575), and 2 mM NaVO$_3$ (Sigma # S-6508) in 10 ml of PBS.

Slit: $10^{-7}$–$10^{-5}$ M biotinylated Slit in PBS.

B. Preparation of assay plates

Coat with 120 μl of stock N-Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 10 μl compound or extract.

Add 10 μl $^{33}$P-Robo (20–25,000 cpm/0.1–10 pmoles/well =$10^{-9}$–$10^{-7}$ M final conc).

Shake at 25° C. for 15 minutes.

Incubate additional 45 minutes at 25° C.

Add 40 μM biotinylated Slit (0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls for all assays (located on each plate)

a. Non-specific binding b. Soluble (non-biotinylated Slit) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant polynucleotide comprising a coding sequence encoding a polypeptide comprising at least one sequence selected from the group consisting of SEQ ID NOS:2–6, 8 and 10–14, or a subsequence thereof having at least 16 consecutive amino acid residues thereof and comprising one or more unboxed amino acid residues of the corresponding sequence in at least one table selected from the group consisting of Table 1 and Table 2, said coding sequence flanked by fewer than 500 bp of native flanking sequence.

2. A recombinant polynucleotide according to claim 1, said polypeptide comprising at least one sequence selected from the group consisting of SEQ ID NOS:2–6, 8 and 10–14, or a subsequence thereof having at least 64 consecutive amino acid residues thereof and comprising one or more unboxed amino acid residues of the corresponding sequence in at least one table selected from the group consisting of Table 1 and Table 2.

3. A recombinant polynucleotide comprising a coding sequence encoding a polypeptide comprising at least one sequence selected from the group consisting of SEQ ID NOS:2–6 and 8–14.

4. A recombinant polynucleotide according to claim 1, said polypeptide comprising at least one sequence selected from the group consisting of SEQ ID NOS:2–6, or a subsequence thereof having at least 16 consecutive amino acid residues thereof and comprising one or more unboxed amino acid residues of the corresponding sequence in at least one table selected from the group consisting of Table 1 and Table 2.

5. A recombinant polynucleotide according to claim 1, said polypeptide comprising SEQ ID NO:2, 3, 4, 5, or 6, or a subsequence thereof having at least 64 consecutive amino acid residues thereof and comprising one or more unboxed amino acid residues of the corresponding sequence in at least one table selected from the group consisting of Table 1 and Table 2.

6. A recombinant polynucleotide according to claim 1, said polypeptide comprising SEQ ID NO:2, or a subsequence thereof having at least 16 consecutive amino acid residues thereof and comprising one or more unboxed amino acid residues of the corresponding sequence in Table 2.

7. A recombinant polynucleotide according to claim 1, said polypeptide comprising SEQ ID NO:2, or a subsequence thereof having at least 64 consecutive amino acid residues thereof and comprising one or more unboxed amino acid residues of the corresponding sequence in Table 2.

8. A recombinant polynucleotide according to claim 1, said polypeptide comprising SEQ ID NO:2.

9. A recombinant polynucleotide according to claim 1, said polypeptide comprising at least one sequence selected from the group consisting of SEQ ID NO:2, amino acid residues 1–10; SEQ ID NO:2, amino acid residues 29–41; SEQ ID NO:2, amino acid residues 75–87; SEQ ID NO:2, amino acid residues 132–141; SEQ ID NO:2, amino acid residues 192–205; SEQ ID NO:2, amino acid residues 258–269; SEQ ID NO:2, amino acid residues 295–311; SEQ ID NO:2, amino acid residues 316–330; SEQ ID NO:2, amino acid residues 373–382; SEQ ID NO:2, amino acid residues 403–422; SEQ ID NO:2, amino acid residues 474–485; SEQ ID NO:2, amino acid residues 561–576; SEQ ID NO:2, amino acid residues 683–697; SEQ ID NO:2, amino acid residues 768–777; SEQ ID NO:2, amino acid residues 798–813; SEQ ID NO:2, ammo acid residues 882–894; SEQ ID NO:2, amino acid residues 934–946; SEQ ID NO:2, amino acid residues 1054–1067; SEQ ID NO:2, amino acid residues 1181–1192; SEQ ID NO:2, amino acid residues 1273–1299; SEQ ID NO:2, amino acid residues 1383–1397; SEQ ID NO:2, amino acid residues 1468–1477; and SEQ ID NO:2, amino acid residues 1508–1517.

10. A recombinant polynucleotide comprising a coding sequence encoding a polypeptide comprising at least one sequence selected from the group consisting of SEQ ID NOS:2–6 and 10–14, or a subsequence thereof having at least 16 consecutive amino acid residues thereof and comprising one or more unboxed amino acid residues of the corresponding sequence in at least one table selected from the group consisting of Table 1 and Table 2, said coding sequence flanked by fewer than 500 bp of native flanking sequence.

11. A recombinant polynucleotide according to claim 10, said polypeptide comprising at least one sequence selected from the group consisting of SEQ ID NOS:2–6 and 10–14, or a subsequence thereof having at least 64 consecutive amino acid residues thereof and comprising one or more unboxed amino acid residues of the corresponding sequence in at least one table selected from the group consisting of Table 1 and Table 2.

12. A recombinant polynucleotide according to claim 10, said polypeptide comprising at least one sequence selected from the group consisting of SEQ ID NOS:2–6 and 10–14.

13. A method of making a polypeptide, comprising the step of translating a polynucleotide according to claim 1.

14. A method of making a polypeptide, comprising the step of translating a polynucleotide according to claim 3.

15. A method of making a polypeptide, comprising the step of translating a polynucleotide according to claim 10.

16. A recombinant polynucleotide comprising a strand of SEQ ID NO:01, or a fragment thereof having at least 24 consecutive nucleotides thereof, and sufficient to specifically hybridize under stringent conditions with a polynucleotide having the sequence defined by the corresponding opposite strand of SEQ ID NO:01, said strand or fragment thereof flanked by fewer than 500 bp of native flanking sequence, said stringent conditions consisting of a hybridization buffer of 30% formamide in 5× SSPE (0.18 MNaCl, 0.01M NaPO$_4$, pH7.7, 0.001M EDTA) buffer at a temperature of 42° C. and a wash buffer of 0.2× SSPE at 42° C., and, said fragment comprising at least one sequence selected from the group consisting of:

| | |
|---|---|
| SEQ ID NO:01, nucl. 1–47; | SEQ ID NO:01, nucl. 1147–1163; |
| SEQ ID NO:01, nucl. 58–99; | SEQ ID NO:01, nucl. 1258–1279; |
| SEQ ID NO:01, nucl. 95–138; | SEQ ID NO:01, nucl. 1375–1389; |
| SEQ ID NO:01, nucl. 181–220; | SEQ ID NO:01, nucl. 1581–1595; |
| SEQ ID NO:01, nucl. 261–299; | SEQ ID NO:01, nucl. 1621–1639; |
| SEQ ID NO:01, nucl. 274–315; | SEQ ID NO:01, nucl. 1744–1755; |
| SEQ ID NO:01, nucl. 351–389; | SEQ ID NO:01, nucl. 1951–1969; |
| SEQ ID NO:01, nucl. 450–593; | SEQ ID NO:01, nucl. 2150–2163; |
| SEQ ID NO:01, nucl. 524–546; | SEQ ID NO:01, nucl. 2524–2546; |
| SEQ ID NO:01, nucl. 561–608; | SEQ ID NO:01, nucl. 2761–2780; |
| SEQ ID NO:01, nucl. 689–727; | SEQ ID NO:01, nucl. 2989–2999; |
| SEQ ID NO:01, nucl. 708–737; | SEQ ID NO:01, nucl. 3108–3117; |
| SEQ ID NO:01, nucl. 738–801; | SEQ ID NO:01, nucl. 3338–3351; |
| SEQ ID NO:01, nucl. 805–854; | SEQ ID NO:01, nucl. 3505–3514; |
| SEQ ID NO:01, nucl. 855–907; | SEQ ID NO:01, nucl. 4010–4025; and |
| SEQ ID NO:01, nucl. 910–953; | SEQ ID NO:01, nucl. 4207–4219. |
| SEQ ID NO:01, nucl. 1007–1059; | |

17. A recombinant polynucleotide according to claim 16, said fragment having at least 36 consecutive residues of SEQ ID NO:01.

18. A recombinant polynucleotide according to claim 16, said fragment having at least 72 consecutive residues of SEQ ID NO:01.

19. A recombinant polynucleotide according to claim 16, said fragment having at least 144 consecutive residues of SEQ ID NO:01.

* * * * *